US008476200B2

(12) United States Patent
Russwurm et al.

(10) Patent No.: US 8,476,200 B2
(45) Date of Patent: Jul. 2, 2013

(54) METHOD FOR DIFFERENTIATING BETWEEN THE NON-INFECTIOUS AND INFECTIOUS CAUSES OF MULTIPLE ORGAN FAILURE

(75) Inventors: Stefan Russwurm, Jena (DE); Konrad Reinhart, Jena (DE)

(73) Assignee: SIRS-Lab GmbH, Jena (DE)

( * ) Notice: Subject to any disclaimer, the term of this patent is extended or adjusted under 35 U.S.C. 154(b) by 942 days.

(21) Appl. No.: 11/577,102

(22) PCT Filed: Aug. 18, 2005

(86) PCT No.: PCT/EP2005/008969
§ 371 (c)(1),
(2), (4) Date: Nov. 24, 2008

(87) PCT Pub. No.: WO2006/042581
PCT Pub. Date: Apr. 27, 2006

(65) Prior Publication Data
US 2009/0075831 A1    Mar. 19, 2009

(30) Foreign Application Priority Data
Oct. 13, 2004    (DE) .......................... 10 2004 049 897

(51) Int. Cl.
*C12Q 1/68*    (2006.01)
(52) U.S. Cl.
USPC ........................................................... 506/9
(58) Field of Classification Search
None
See application file for complete search history.

(56) References Cited

U.S. PATENT DOCUMENTS

| 5,830,679 A | 11/1998 | Bianchi et al. |
| 2001/0051344 A1 | 12/2001 | Shalon et al. |
| 2002/0164656 A1 | 11/2002 | Hoeffler |
| 2003/0194752 A1 | 10/2003 | Anderson et al. |
| 2004/0096917 A1 | 5/2004 | Ivey et al. |
| 2004/0106142 A1 | 6/2004 | Ivey et al. |
| 2005/0228172 A9* | 10/2005 | Wang ........................... 536/24.3 |
| 2006/0134685 A1 | 6/2006 | Zipfel et al. |
| 2008/0070235 A1 | 3/2008 | Russwurm et al. |
| 2008/0286763 A1 | 11/2008 | Russwurm |
| 2009/0325152 A1 | 12/2009 | Russwurm et al. |
| 2011/0076685 A1* | 3/2011 | Moeller et al. ..................... 435/6 |

FOREIGN PATENT DOCUMENTS

| DE | 10041215 A1 | 10/2001 |
| EP | 1270740 A1 | 1/2003 |
| WO | WO 99/40434 A1 | 8/1999 |
| WO | 03002763 A1 | 1/2003 |
| WO | WO 03/002763 A1 | 1/2003 |
| WO | WO 2004/031412 A2 | 4/2004 |
| WO | 2004043236 A2 | 5/2004 |
| WO | WO 2004/067778 A2 | 8/2004 |
| WO | WO 2004/087949 A2 | 10/2004 |
| WO | WO2004087949 * | 10/2004 |

OTHER PUBLICATIONS

Gitig, Diana (Genetic Engineering and Biotechnology New, vol. 31, No. 20, pp. 1-3, Nov. 2011).*
Cheung, Nature Genetics 2003, vol. 33, p. 422-425.*
Thisted,pp. 1-6. Ronald A. et al.: "What is a P-value?", (1998) available from http:l/www.stat.uchicago.edu/thisted, printed.*
Cobb et al. (2004, Crit Care Med, 2002, 30(12):2711-2721).*
Feezor et al (Clinical Infectious Diseases, 2005, vol. 41, pp. S427-S435).*
Gitig, Diana (Genetic Engineering and Biotechnology New, vol. 31, No. 20, pp. 1-3, Nov. 2011.*
Bonaldo et al. (Gen Res., 1996, 6, p. 791-806).*
Office Action in corresponding chinese application procedure.
Enard et al. (Science 2002 vol. 296 p. 340).
Wu (Journal of pathology 2001 vol. 195 p. 53).
Newton et al (Journal of Computational Biology 2001 vol. 8 p. 37).
Hynninen et al. (Shock 2003 vol. 20 p. 1).
Perry et al. (Intensive Care Med 2003 Vo. 29 p. 1245).
Riedemann et al. (Journal of Clinical Investigation Jul. 2002 vol. 110 p. 101).
Tulzo et al. "Early Circulating Lymphocyte Adoptosis in Human Septic Shock is Associated With Poor Outcome" Shock 2002, vol. 18, p. 487-494.
Freezor et al., Clinical Infectious Disease, vol. 41, S427-S435, Sep. 2005.
Gitig, Diana, Genetic Engineering & Biotechnology News, vol. 31, No. 20, pp. 1-3, Nov. 15, 2011.
Van De Vijver, M.J. et al.: "A gene-expression signature as a predictor of survival in breast cancer" N. Engl. J. Med (2002) 347 (25) 1999-2009.
Hoshikawa, Y. et al.: "Hypoxia induces different genes in the lungs of rats compared with mice", Physiol Genomics (2003) 12 : 209-219.
Cheung, V.G. et al.: "Natural variation in human gene expression assessed in lymphoblastoid cells", Nature Genetics (2003), vol. 33, pp. 422-425.
Thisted, Ronald A. et al.: "What is a P-value?", (1998) available from http://www.stat.uchicago.edu/thisted, printed pp. 1-6.
Database NETAFFX, Mar. 15, 2006, http://www.affymetrix.com/analysis/netaffx/probematch/probe_match.affx?netaffx=netaffx4_annot.
Ray, Arghya et al.: "Peptide nucleic acid (PNA): its medical and biotechnical applications and promise for the future", Department of Physical Chemistry, Chalmers University of Technology, S 412 96 Gothenburg, 2000, Medical and Biotechnical Applications of PNA, 14:1041-1060.

(Continued)

*Primary Examiner* — Stephanie K Mummert
(74) *Attorney, Agent, or Firm* — Patent Central LLC; Stephan A. Pendorf

(57) ABSTRACT

The present invention relates to the use of gene expression profiles obtained in vitro from patient samples for differentiating between the non-infectious and infectious causes of multiple organ failure. The invention also relates to a method for measuring gene expression profiles in vitro and the use of said gene expression profiles and/or of the probes used therein for screening active substances against the non-infectious and/or infectious causes of multiple organ failure.

20 Claims, No Drawings

OTHER PUBLICATIONS

Jansen, Burkhard et al.: "Antisense therapy for cancer—the time of truth", Nov. 2002, The Lancet Oncology, 3:672-683.
Galderisi, Umberto et al.: "Antisense Oligonucleotides as Therapeutic Agents", 1999, Journal of Cellular Physiology, 181:251-257.
Riesewijk, Anne at al.: "Gene expression profiling of human endometrial receptivity on days LH+2 versus LH+7 by microarray technology", 2003, 9(5):253-264.
Liu, Zheng et al.: "Gene expression profiles in human nasal polyp tissues studied by means of DNA microarray", 2004, 114(4):783-790.
Cobb, J. Perren. Crit Care Med 2002 vol. 30, No. 12. p. 2711-2721.
"Details for HG-U95AV2:2024_S_AT" Internet Citation [Online], Oct. 1, 2004, pp. 1-3, XP007907827, found on the internet: URL: https://www.affymetrix.com/analysis/netaffx/fullrecord.affx?pk= H>, found on Mar. 20, 2009.
Haslinger, Christian et al.: "Microarray Gene Expression Profiling of B-Cell Chronic Lymphocytic Leukemia Subgroups Defined by Genomic Aberrations and VH Mutation Status", Journal of Clinical Oncology, American Society of Clinical Oncology, US, Bd. 22, Nr. 19, Oct. 1, 2004, pp. 3937-3949, XP009114229.*Summary*. *p. 3938, right column.*.
Japanese Office Action and English Translation Thereof, Apr. 26, 2011.
"Method of Measuring Procalcitonin" Examination and Technology 2002, vol. 30, No. 7, pp. 569-570.
Cobb, et al. "Sepsis Gene Expression Profiling: Murine Splenic Compared With Hepatic Responses Determined by Using Complementary DNA Microarrays" Crit. Care Med., 2002, vol. 30, pp. 2711-2721.
Liu, et al. "Gene Expression Profiles in Human Nasal Polyp Tissues Studied by Means of DNA Microarray" J. Allergy Clin. Immunol., 2004, vol. 114, pp. 783-790.
Natanson, et al., "Anti-inflammatory Therapies to Treat Sepsis and Septic Shock: A Reassessment," Natl. Inst. Health, Bethesda, MD. (1997).
Knaus et al., "Prognosis in Acute Organ-System Failure," The George Washington University Medical Center, Washington, DC, 685-693, Dec. 1985.
Alizadeh, "Distinct Types of Diffuse Large B-Cell Lymphoma Identified by Gene Expression Profiling," Nature, 403: 503-511 (2000).
American College of Chest Physicians/Society of Critical Care Medicine Consensus Conference: Definitions for Sepsis and Organ Failure and Guidelines for the use of Innovative Therapies in Sepsis, Crit. Care Med., 20:6, 864-874 (1992).
Bernardin et al., "Blood Pressure and Arterial Lactate Level are Early Indicators of Short-Term Survival in Human Septic Shock," Intensive Care Med., 22: 17-25 (1996).
Feezor et al., "Genomic and Proteomic Determinants of Outcome in Patients Undergoing Thoracoabdominal Aortic Aneurysm Repair," J. of Immun., 172: 7103-109 (2004).
Duswald et al., "Released Granulocytic Elastawe: An Indicator of Pathobiochemical Alterations in Septicemia after Abdominal Surgery," Surgery, 892-899, 1985.
Fodor et al., Light-Directed, Spatially Addressable Parallel Chemical Synthesis, Science, 251: 767-773 (1991).
Gillespie et al., "A Quantitative Assay for DNA-RNA Hybrids with DNA Immobilized on a Membrane," J. Mol. Biol., 12: 829-842 (1965).
Golub, "Molecular Classification of Cancer: Class Discovery and Class Prediction by Gene Expression Monitoring," Science, 286 : 531-537 (1999).
Goris et al., "Multiple-Organ Failure," Arch. Surg., 120: 1109-1115 (1985).
Hack et al., "Increased Plasma Levels of Interleukin-6 in Sepsis," Blood, 74:5,1704-1710 (1989).
Huber et al., "Parameter Estimation for the Calibration and Variance Stabilization of Microarray Data," Statistical Applications in Genetics & Molecular Biology, 2:1, Article 3, 1-22 (2003).
Kafatos et al., "Determination of Nucleic Acid Sequence Homologies and Relative Concentrations by a Dot Hybridization Procedure," Nucleic Acids Research, 7:6, 1541-1552 (1979).
Lennon et al., Hybridization of Arrayed cDNA Libraries, TIG, 7:10, 314-317 (1991).
Levy et al., "2001 SCCM/ESICM/ACCP/ATS/SIS International Sepsis Definitions Conference," Crit. Care Med., 31:4, 1250-1256 (2003).
Livingston et al., "Multiple Organ Failure: A Common Problem in Surgical Intensive Care Unit Patients," Ann. Med., 27: 13-20 (1995).
Marecaux et al., "Blood Lactate Levels are Better prognostic Indicators than TNF and IL-6 Levels in Patients with Septic Shock," Intensive Care Med., 22: 404-408 (1996).
Marik, "Gastric Intramucosal pH. A Better Predictor of Multi Organ Dysfunction Syndrome and Death than Oxygen-Derived Variables in Patients with Sepsis," Chest, 104: 225-29 (1993).
Nuytinck et al., "Posttraumatic Complications and Inflammatory Mediators," Arch. Surg., 121: 886-890 (1986).
Patel et al., "Interleukin 6 is a Prognostic Indicator of Outcome in Severe Intra-Abdominal Sepsis," British J. of Surgery, 8: 1306-08 (1994).
Pease et al., "Light-Generated Oligonucleotide Arrays for Rapid DNA Sequence Analysis," Proc. Nat'l Acad. Sci., 91: 5022-26 (1994).
Schena et al., "Quantitative Monitoring of Gene Expression Patterns with a Complementary DNA Microarray," Science, 270: 467-470 (1995).
Schlag, et al., Introduction: "Organ in Shock", "Early Organ Failure", "Late Organ Failure," Pathophysiology of Shock, Sepsis, and Organ Failure, Springer-Verlag, 1-3 (1993).
Southern, EM, "An Improved Method for Transferring Nucleotides from Electrophoresis Strips to Thin Layers of Ion-Exchange Cellulose," Anal. Chem., 62: 317-8 (1974).
Vincent, "Prevention and Therapy of Multiple Organ Failure," World J. Surg., 20: 465-470 (1996).
Vincent et al., "The SOFA (Sepsis-Related Organ Failure Assessment) Score to Describe Organ Dysfunction/Failure," Intensive Care Med., 22: 707-710 (1996).
Chinnaiyan, et al., "Molecular Signatures of Sepsis, Multiorgan Gene Expression Profiles of Systemic Inflammation", American Journal of Pathology, 159:4, 1199-1209 (2001).
Yu, et al., "Differential gene expression in gram-negative and gram-positive sepsis", Am J Respir Crit Care Med 169:10, 1135-43 (2004).
Schlag, G., et al., "The cell in shock: the origin of multiple organ failure", Resuscitation 21:2-3, 137-80 (1991).
Database EMBL *Homo sapiens* cDNA clone, Jan. 13, 1996, XP002412098, gefunden im EBI, Database accession No. N32857, Zusammenfassung.
Database EMBL *Homo sapiens* cDNA clone, Jan. 13, 1996, XP002412099, gefunden im EBI, Database accession No. N32853, Zusammenfassung.
Database EMBL *Homo sapiens* cDNA clone, Jan. 13, 1996, XP002412100, gefunden im EBI, Database accession No. N32495, Zusammenfassung.
Database EMBL *Homo sapiens* cDNA clone, Jun. 4, 1999, XP002412101, gefunden im EBI, Database accession No. AI701077, Zusammenfassung.
Database EMBL Human Anti-Hepatitis A Ig Lambda Chain 10, Mar. 10, 1992, XP002412102, gefunden im EBI, Database accession No. M87790, Zusammenfassung.
Database EMBL *Homo sapiens* cDNA clone, Mar. 25, 1999, XP002412103, gefunden im EBI, Database accession No. AI559317, Zusammenfassung.
Database EMBL *Homo sapiens* cDNA clone, Jan. 19, 1996, XP002412104, gefunden im EBI, Database accession No. N34897, Zusammenfassung.
Database EMBL *Homo sapiens* cDNA clone, Apr. 14, 1998, XP002412105, gefunden im EBI, Database accession No. AA907084, Zusammenfassung.
Database EMBL *Homo sapiens* cDNA clone, Feb. 17, 1996, XP002412106, gefunden im EBI, Database accession No. N45223, Zusammenfassung.
Cobb, et al., "Sepsis gene expression profiling; Murine splenic compared with hepatic responses determined by using complimentary DNA microarrays," Crit Care Med 30:12, 2711-2 (2002).

Tsukahara, et al., "Gene Expression in Human Neutrophils During Activation and Priming by Bacterial Lipopolysaccharide", Journal of Cellular Biochemistry, 89:848-861 (2003).

Deigner, 6$^{th}$ World Congress on Trauma, Shock, Inflammation & Sepsis? Pathophysiology, XP002327554, www.sirs lab.de/content/de/pdf/kompetenzen/deinger, (2005).

Pathan, et al., "The Complexity of the Inflammatory Response to Meningococcal Sepsis Revealed by Gene Expression . . .", Crit Care Med, 30:12 Suppl. (2002).

Mira, et al., "Association of TNF2, a TNF-α Promoter Polymorphism, with Septic Shock Susceptibility and Mortality", JAMA 208:6, 561-8 (1999).

Barriere, et al., "An overview of mortality risk prediction in sepsis", Crit Care Med, 23:2, 376-393 (1995).

Botwell, David, D. L., "Options available—from start to finish—for obtaining expression data by microarray", Nature Genetics Supplement, 21: 25-32 (1999).

Prucha, et al., "Expression Profiling: Toward an Application in Sepsis Diagnostics", Shock, 22:1 29-33 (2004).

Weigand, et al., "Gene Expression Pattern in Human Monocytes as a Surrogate Marker for Systemic Inflammatory Response Syndrome (SIRS)", Molecular Medicine, 5:192-202 (1999).

Rowe, et al., "An Array of Immunosensor for Simultaneous Detection of Clinical Analysis," Anal. Chem. 71:433-39 (1999).

Oberhoffer, et al., "Discriminative power of inflammatory markers for prediction of tumor necrosis . . .," Intensive Care Med, 26:S170-S174 (2000).

Database EMBL *Homo sapiens* (clone KT2) Bone Morphogenetic Protein-1 (BMP-1) mRNA & Alternatively Spliced . . . , XP0023073 Database accession No. L35279, Zusammenfassung (1995).

Heller, et al., "Discovery and analysis of inflammatory disease-related genes using cDNA microarrays", Proc. Natl. Acad, Sci USA, 94: 2150-55 (1997).

Pfeiffer, et al., "Endotoxinamie . . . (endotoxemia and multiple organ failure upon polytrauma)," Anaesthesiol Reanimat, 21: 91-96 (1996).

Bone, et al., "The ACCP/SCCM . . . Definitions for sepsis and organ failure and guidelines for the use of innovative therapies . . . ," Chest 101:1656-1662, Crit Care Med, 20:864-874, 1992.

http://chirinn.klinikum.uni-muenchen.de/forschung/for_01_14_04.html, as of Oct. 2004, modifed.

Nast-Kolb, et al., Die Wertigkeit . . . (Valence of biomendial factors with polytrauma), Hefte Unfallheilkunde, 215 (1991).

Natanson, C., "Anti-inflammatory therapies to treat sepsis and septic shock" A reassessment, Crit Care Med, 25: 1095-1099, Jul. 1997.

Geiger, K., "Fruhparameter fur Multiorgandysfunktionssyndrom (early parameters for multiple organ dysfunction syndrome)," Sepsis in der Fruhphase . . . Medizin Verlag 19-25 (1995).

Office Action in corresponding chinese application procedure, Dec. 18, 2009.

EMBL N32857, Publication Date: Jan. 13, 1996.
EMBL N32853, Publication Date: Jan. 13, 1996.
EMBL N32495, Publication Date: Jan. 13, 1996.
EMBL A1701077, Publication Date: Jun. 4, 1999.
EMBL M87790, Publication Date: Mar. 10, 1992.
EMBL A1559317, Publication Date: Mar. 25, 1999.
EMBL N34897, Publication Date: Jan. 19, 1996.
EMBL AA907084, Publication Date: Apr. 14, 1998.
EMBL N45223, Publication Date: Feb. 17, 1996.

Ko, J.L., et al., "Molecular cloning and expression of a fungal immunomodulatory protein, FIP-fve, from Flammulina . . . ," J. of the Formosan Med Assoc. 96:7 517-524 (1997).

Liu, Z., et al., "Gene expression profiles in human nasal polyp tissues studied by means of DNA microarray," J. of Allergy and Clinical Immunology, 114: 4, 783-90 (2004).

Database NETAFIX, "www.affymetrix.com/analysis/netaffx/probematch/probe_match.affx?netaffx=netaffx4_annot" (2006).

Riesewijk, et al., "Gene expression profiling of human endometrial receptivity on days LH+2 versus LH+7 by microarray technology," Mol Human Reprod, 9:5 253-264 (2003).

Lü, Y. et al. "Analysis of the poly-genes expression changes in liver by gene expression profile chip in gut ischemia-reperfusion rats" Zhonggui Wei Zhong Bing Ji Jiu Yi Xue, Feb. 2003;15(2)84-7 www.ncbi.nim.nih.gov.

Liao, JK et al. "Change of nuclear factor-kappaB activity in early burn injury and its significance" Zhonggui Wei Zhong Bing Ji Jiu Yi Xue, Apr. 2003 15 (4) 220-1 www.ncbi.nim.nih.gov.

Power, C. et al. "Proinflammatory Effects of Bacterial Lipoprotein on Human Neutrophil Activation Status, Function and Cytotoxic Potential In Vitro" Shock, 2001, vol. 15, No. 6, pp. 461-466.

* cited by examiner

METHOD FOR DIFFERENTIATING BETWEEN THE NON-INFECTIOUS AND INFECTIOUS CAUSES OF MULTIPLE ORGAN FAILURE

The present invention relates to the use of gene expression profiles obtained in vitro from a patient sample for differentiating between the non-infectious and infectious causes of multiple organ failure, a method for measuring such gene expression profiles in vitro, as well as the use of gene expression profiles and/or of the probes used therein for switching off and/or changing activity of target genes and/or detecting gene activity for screening active substances against non-infectious/infectious multiple organ failure and/or for assessing therapeutic effects of active substances for non-infectious/infectious multiple organ failure.

The present invention further relates to new possibilities of differentiating between non-infectious and infectious causes of multiple organ failure of patients, which can be derived from experimentally verified insights in conjunction with the occurrence of changes in gene activity (transcription) in patients with multiple organ failure.

Despite advances in pathophysiological understanding and the supportive treatment, the multiple organ failure syndrome (MOFS) and multiple organ failure (MOF), respectively, is the most frequent cause of death in patients in intensive care and is continuously increasing worldwide. The consequences of this development are not only considerable to the individual patient but they also have enormous effects on the costs of the public health care systems and the medical progress in many fields of medicine.

Multiple organ failure is defined as the failure of two or more vital organ systems occurring simultaneously or within a short time period. The multiple organ failure syndrome (MOFS) precedes the MOF as initial organ insufficiency [1]. Today's definition of multiple organ failure is the dysfunction of two or more organs occurring simultaneously or within a short period of time, whereas a chronically persistent organ failure can be ruled out [2]. The prognosis of MOF is closely related to the number of the involved organ systems. If one organ fails, the mortality rate within 24 hours is 22%; after 7 days it is 41%. In the case of failure of three organ systems, the mortality increases on the first day to 80% and after 4 days to 100% [3].

For the clinical scoring of the degree of severity in MOFS and MOF, the multiple organ failure score (MOF-score) of GORIS et al. [4] or, alternatively, the sepsis related organ failure assessment (SOFA) score are routinely used [5]. The MOF score renders a quick and clinically simple classification of the organ function in three grades possible. In the clinical literature, a MOF score>4 is routinely described as MOF [6]. SOFA score is a point system quickly scoring the clinical assessment of the function of the following organ systems: respiration (lung), coagulation, liver, cardiovascular system, central nervous system and kidney. Four grades are used in this scoring system.

Clinically, the MOF runs in three stages [7]:
1. Organ in shock: The triggering pathophysiological mechanism is a perfusion deficiency of very different genesis. This happens within hours and does not yet lead to permanent damages.
2. Organ dysfunction: If the persistent perfusion deficit persists for the next few days, this will lead to the development of SIRS (Systemic Inflammatory Response Syndrome, classified according to [8]) with local oedema and cell damages. This stage is called multiple organ dysfunction syndrome (MODS).
3. Organ failure: The persistent perfusion deficit leads to stasis in the splanchnic area which leads to a superinfection and translocation of endotoxins from the intestines. This leads to a potentiation of the clinical symptoms and to the complete picture of the sepsis. The organ dysfunction becomes an organ failure.

MODS and MOF are clinical pictures with a complex pathophysiology. The exact molecular causes for the development and the complexity of the immunological-inflammatory host response to severe infection and trauma that MODS and MOF can be both of infectiologic and non-infectiologic genesis. MODS and MOF routinely develop as a clinical important complication in patients with sepsis, after a shock that was caused by trauma, with patients after surgeries where the heart-lung machine was used, after organ transplantation, and others. An important pathogenetic mechanism for the development of MODS and MOF is the development of a systemic inflammatory syndrome (SIRS, [8]). The pathophysiological processes initiated in connection with SIRS do not only involve all components of the immune system, but interfere with all levels of the cardiocirculatory system and are not restricted to myocardial depression and vasodilation. The cardiocirculatory changes in particular on the microcirculation level form the common final distance and result in a tissue hypoxia which is considered an important cofactor in the pathogenesis of multiple organ failure.

MODS and MOF can be both of infectiologic and non-infectiologic genesis. MODS and MOF routinely develop as a clinical important complication in patients with sepsis, after a shock that was caused by trauma, with patients after surgeries where the heart-lung machine was used, after organ transplantation, and others (FIG. 1). An important pathogenetic mechanism for the development of MODS and MOF is the development of a systemic inflammatory syndrome (SIRS, [8]). The pathophysiological processes initiated in connection with SIRS do not only involve all components of the immune system, but interfere with all levels of the cardiocirculatory system and are not restricted to myocardial depression and vasodilation. The cardiocirculatory changes in particular on the microcirculation level form the common final distance and result in a tissue hypoxia which is considered an important cofactor in the pathogenesis of multiple organ failure.

By today's standards, the most important mechanisms of the development of MODS and MOF [10]: It seems that an overactive immune system plays a decisive role in the development of multiple organ failure. In this context, the endothelium plays a central key role by secretion of cytokines and by imparting leukocyte adhesion. Signal transduction cascades are activated in the endothelial cells leading to the expression and activation of transcription factors.

The reason why there is still no sensitive/specific diagnostic being able to differentiate between infectious and non-infectious causes is the still incomplete knowledge of the early stage processes in MODS and MOF. New types of biomarkers and diagnostics, now even on a gene expression level, may provide the essential diagnostic information for early diagnosis of multiple organ failure as well as for the differentiation between infectious and non-infectious causes of MODS and MOF. Additionally, they are important in contributing to the clarification of the pathophysiologic mechanisms of systemic inflammations.

The precursory symptoms that are often used in clinical practice, as fever, leucocytosis, tachycardia and tachypnea are completely unspecific for the diagnosis of MODS or MOF as well as for differentiating between infectious and non-infectious causes of MODS and MOF. Parameters detecting irregularities in microcirculations at an early stage, as for example changes in the pH of the intestinal mucosa [11] and lactate level in the capillary bed [12, 13], emerging of a respiratory insufficiency the cause of which is not in the lung [2], the ascent of the leucocyte elastase [14, 15], the height of the neopterine level [16], the activation of polymorphnuclear leucocytes and the height of the IL-6-level [17] are suitable as early parameters for the later development of MODS and MOF only to a limited extend, but they cannot contribute to the differentiation between infectious and non-infectious causes of MODS and MOF. Thus, there is urgent need for novel diagnostic methods for improving the capacity of the person skilled in the art to differentiate at an early stage between non-infectious and infectious MODS or MOF and to make predictions on how the patient will respond to specific treatments.

However, it is exactly the differentiation between infectious and non-infectious causes of MODS and MOF which is of utmost medicinal importance, as for example antibiotics may be used more efficiently with this differentiation, this contributing to considerable cost savings as well as to the avoidance of side effects caused by the unspecific application of antibiotics. In the case of non-infectious MODS or MOF it is, additionally, possible to avoid time and people-intensive diagnostic measures that are very stressful for the patient (e.g. transport to CT/MRI) for identification of the respective site of infection, the realisation of comprehensive microbiological methods (e.g. examination of blood cultures for which the patient also must deliver great amounts of blood) but also the risky exchange of all plastics material connected with the patient, such as venous catheter, etc. Vice versa, the quick identification of infectious causes of MODS or MOF can ensure that these measures are taken quickly and mortality can, therefore, be reduced.

Technological advances, in particular the development of microarray technology, make it now possible for the person skilled in the art to simultaneously compare 10 000 or more genes and their gene products. The use of such microarray technologies can now provide information regarding the status of health, regulatory mechanisms, biochemical interactions and signal transmitter networks. As the comprehension how an organism reacts to infections is improved this way, this should faciliate the development of enhanced modalities of detection, diagnosis and therapy of sepsis disorders.

Microarrays have their origin in "Southern blotting" [19], which represented the first approach to immobilizing DNA-molecules so that it can be addressed three-dimensionally on a solid matrix. The first micro arrays consisted of DNA-fragments, frequently with unknown sequence, and were applied dotwise onto a porous membrane (normally nylon). Routinely, cDNA, genomic DNA or plasmid libraries were employed and the hybridized material was labelled with a radioactive group [20-22].

Recently, the use of glass as substrate and fluorescence for detection together with the development of new technologies for the synthesis and for the application of nucleic acids in very high densities made it possible to miniaturize the nucleic acid arrays. At the same time, the experimental throughput and the information content were increased [23-25].

Further, it is known from WO 03/002763 that microarrays basically can be used for the diagnosis of sepsis and sepsis-like conditions.

The first explanation for the applicability of microarray technology was obtained through clinical trials in the field of cancer research. Here, expression profiles proofed to be valuable with regard to identification of activities of individual genes or groups of genes, which correlate with certain clinical phenotypes [26]. Many samples of individuals with or without acute leukaemia or diffuse B-cell lymphoma were analyzed and gene expression labels (RNA) were found and subsequently employed for the clinically relevant classification of these types of cancer [26,27]. Golub et al. found out that an individual gene is not enough to make reliable predictions, while, however, predictions based on the change in transcription of 53 genes (selected from more than 6000 genes, which were present on the arrays) are highly accurate [26].

Alisadeh et al. [27] examined large B-cell lymphomas (DLBCL). Expression profiles were worked up by the authors with a "lympochip", a microarray bearing 18 000 clones of complementary DNA that was developed to monitor genes that are involved in normal and abnormal development of lymphocytes. By using cluster analysis, they managed to classify DLBCL in two categories that showed great differences with regard to the survival chance of patients. The gene expression profiles of these subtypes correlated to two significant stages of the B-cell differentiation.

The Applicant's German patent applications DE 103 40 395.7, DE 103 36 511.7, DE 103 150 31.5 and 10 2004 009 952.9 which have not yet been prepublished, describe that gene expression profiles are, in principle, usable, for example by means of microarray technology for the diagnosis of SIRS, generalised inflammatory inflammations, sepsis and severe sepsis. These applications are herein incorporated by reference.

It is known from Feezor et al. [28] that the gene activities of patients who developed SIRS with multiple organ dysfunction syndrome (MODS) as a consequence of their surgical treatment differ from those of patients who developed SIRS without MODS as a consequence of the same surgical treatment. However, these studies do not allow a statement on the differentiation of non-infectious MOF compared to infectious MOF, as the patients did not show an infection.

The use of gene expression profiles for the differentiation between non-infectious MOF and infectious MOF was not yet described.

The invention disclosed in the present application is basing on the perception that the gene activities of patients with non-infectious MOF differs from the gene activities of patients with infectious MOF. Thus, these differences in gene activities allow for the differentiation between infectious and non-infectious MOF by means of gene expression. The conventionally used clinical parameters do not allow such a differentiation, which, however, is very important for the initiation of a specialised therapy in intensive care.

Thus, it is the object of the present invention to differentiate between non-infectious MOF and infectious MOF by means of gene activity markers.

The present invention relates in particular to the use of gene expression profiles that have been obtained in vitro from a patient sample for the differentiation between non-infectious and infectious causes of multiple organ failure.

The present invention is further usable for assessing the course of patients suffering from non-infectious and infectious causes of multiple organ failure during therapy.

The present invention is further usable as inclusion or exclusion criterion of patients with non-infectious or infectious causes of multiple organ failure in clinical trials of the stages 2-4.

A preferred embodiment of the present invention is the creation of gene activity data for further electronic processing as well as for the production of software for the description of the individual prognosis for a sepsis patient, for diagnosis and/or patient data management systems.

The present invention may also be used for the creation of "in silico" expert systems and/or for "in silico" modulation of cellular ways of signal transfer.

For the creation of gene expression profiles according to the present invention, a majority of specific genes and/or gene fragments is used, selected from the group consisting of SEQ ID NO: 1 to SEQ ID NO: 1297, as well as gene fragments thereof with 5-2000 or more, preferably 20-200, more preferably 20-80 nucleotides.

These sequences with the SEQ ID NO: 1 to SEQ ID NO: are incorporated by the scope of the present invention and they are in detail disclosed in the enclosed sequence listing comprising 1297 sequences which is, thus, part of the description of the present invention and, therefore, also part of the disclosure of the invention. In the sequence listing the individual sequences with sequence ID No. SEQ ID NO: 1 to SEQ ID NO: 1297 are further assigned to their GenBank Accession No.

The present invention further relates to the use of gene expression profiles, which are obtained in vitro from a patient sample, and/or of probes used for this purpose, selected from the group consisting of SEQ ID NO: 1 to SEQ ID NO: 1297 as well as gene fragments thereof with at least 5-2000, preferably 20-80 nucleotides, for switching off and/or for changing the activity of target genes and/or the determination of the gene activity for the screening of active substances for non-infectious/infectious multiple organ failure and/or for assessing the effect on non-infectious/infectious multiple organ failure.

In this context, also hybridisable synthetic analogues of the listed probes may be used.

Further, the gene activities in patients suffering from non-infectious or infectious causes of multiple organ failure can be determined in clinical studies of the stages 2-4 in a biologic fluid and from this "value" conclusions may be drawn with regard to the course of disease, the chance of survival, the course of therapy or the possibility to include or exclude the sepsis patients in clinical trials.

Another embodiment of the invention is characterized in that a specific gene and/or gene fragment selected from the group consisting of SEQ ID NO: 1 to SEQ ID NO: 1297, as well as gene fragments thereof with 5-2000 or more, preferably 20-200, more preferably 20-80 nucleotides.

Another embodiment of the present invention is characterized in that at least 2 to 100 different genes and/or gene fragments are used.

Another embodiment of the present invention is characterized in that at least 200 different genes and/or gene fragments are used.

Another embodiment of the present invention is characterized in that at least 200 to 500 different genes and/or gene fragments are used.

Another embodiment of the present invention is characterized in that at least 500 to 1000 different genes and/or gene fragments are used.

Another embodiment of the present invention is characterized in that at least 1000 to 2000 different genes and/or gene fragments are used.

Another embodiment of the present invention is characterized in that the genes or gene fragments and/or the sequences derived from their RNA are replaced by synthetic analogues, aptamers, as well as peptide nucleic acids.

Another embodiment of the invention is characterized in that the synthetic analog of the genes comprise 5-100, in particular approx. 70 base pairs.

Another embodiment of the present invention is characterized in that the gene activity is determined by means of hybridisation methods.

Another embodiment of the present invention is characterized in that the gene activity is determined by means of microarrays.

Another embodiment of the invention is characterized in that the gene activity is determined by hybridisation-independent methods, in particular by enzymatic and/or chemical hydrolysis and/or amplification methods, preferably PCR, subsequent quantification of nucleic acids and/or of derivates and/or fragments of same.

Another embodiment of the present invention is characterized in that the sample is selected from: body fluids, in particular blood, liquor, urine, ascitic fluid, seminal fluid, saliva, puncture fluid, cell content, or a mixture thereof.

Another embodiment of the present invention is characterized in that cell samples are subjected a lytic treatment, if necessary, in order to free their cell contents.

It is obvious to the person skilled in the art that the individual features of the present invention shown in the claims can be combined with each other in any desired way.

The term marker genes as used in the present invention encompasses all derived DNA-sequences, partial sequences and synthetic analogues (for example peptido-nucleic acids, PNA). The description of the invention referring to the determination of the gene expression on RNA level is not supposed to be a restriction but only an exemplary application of the present invention.

The description of the invention referring to blood is only an exemplary embodiment of the present invention. The term biological liquids as used in the present invention encompasses all human body fluids.

Further advantages and features of the present invention will become apparent from the description of the embodiment as well as from the drawing.

EMBODIMENT

Differential gene expression examinations for differentiating between the non-infectious and infectious causes of multiple organ failure.

Whole blood samples of 57 patients who were under the care of a surgical intensive care unit were examined for the measurement of the differential gene expression for differentiating between non-infectious and infectious causes of multiple organ failure.

Whole blood samples of 31 patients who developed an infectious MOF [then called severe sepsis or septical shock and classified according to 8] within the care of a surgical intensive care unit.

Furthermore, whole blood samples were drawn from 26 patients who developed a non-infectious MOF [classified according to 8] within the care of a surgical intensive care unit.

As reference samples the total RNA from the cell lines SIG-M5 were used.

A range of characteristics of both patient groups is shown in table 1. In the table, information regarding age, sex, as well as the SOFA-score as measurement for the function of the organ systems is given. Likewise, the plasma protein level of procalcitonin (PCT) and CRP, the number of leucocytes as well as the most usual CDC (Center of Disease Control) criteria of the patients are indicated.

All of the patient samples were co-hybridised with the reference sample on one microarray each.

TABLE 1

Data of the group of patients

| | Patients with infectious MOF | Patients with non-infectious MOF |
|---|---|---|
| Number | 31 | 26 |
| Sex m/f | 17/14 | 15/11 |
| Age* [years] | 60 (17) | 69 (10) |
| APACHE-II-Score* [points] | 14 (10) | 14.9 (3.4) |
| SOFA-Score* [points] | 10 (3) | 8 (3) |
| Number of OD* | 3 (1) | 3 (1) |
| PCT* [ng/ml] | 3.1 (7.7) | 3.8 (6.7) |
| CRP* [µg/l] | 188 (168) | 80.2 (90.2) |
| Leucocytes* [No./l] | 13.00 (8 150) | 12.300 (6925) |
| Kind of infection according to CDC criterion | | |
| Pneumonia | 15 patients | none |
| Intraabdominal infection | 13 patients | |
| Infection of operating site without wound infection | 2 patients | |
| Infection of the gastrointestinal tract | 1 patient | |

*Median (interquartile distance)

Experimental Description:

After drawing whole blood, the total RNA of the samples was isolated using the PAXGene Blood RNA kit according to the manufacturer's (Qiagen) instructions.

Cell Cultivation

For cell cultivation (control samples) 19 cryo cell cultures (SIGM5) (frozen in liquid nitrogen) were used. The cells were each inoculated with 2 ml Iscove's medium (Biochrom AG) supplemented with 20% fetal calf serum (FCS). Subsequently, the cell cultures were incubated in 12 well plates for 24 hours at 37° C. in 5% $CO_2$. Subsequently, the content of the 18 wells was parted in 2 parts with the same volume so that finally 3 plates of the same format (36 wells in total) were available. Afterwards, the cultivation was continued under the same conditions for 24 hours. Afterwards, the resulting cultures of 11 wells of each plate were combined and centrifuged (1000×g, 5 min, ambient temperature). The supernatant was removed and the cell pellet was dissolved in 40 ml of the above mentioned medium. These 40 ml of dissolved cells were distributed in equal shares in two 250 ml flasks and incubated after adding 5 ml of the above-mentioned medium. 80 µl of the remaining 2 ml of the two remaining plates were placed in empty wells of the same plates that had previously been prepared with 1 ml of the above-mentioned medium. After 48 hours of incubation, only one of the 12 well plates was processed as follows: 500 µl were extracted from each well and combined. The resulting 6 ml were introduced into a 250 ml flask comprising approximately 10 ml of fresh medium. This mixture was centrifuged 5 minutes with 1000×g at ambient temperature and dissolved in 10 ml of the above-mentioned medium. The following results were obtained by subsequent counting of cells: 1.5×107 cells per ml, 10 ml total volume, total number of cells: 1.5×108. As the number of cells was not yet sufficient, 2.5 ml of the above-mentioned cell suspension was introduced into 30 ml of the above-mentioned medium in a 250 ml (75 $cm^2$) flask (4 flasks in total). After 72 hours of incubation 20 ml of fresh medium were added to each flask. After the subsequent incubation of 24 hours, the cells were counted as described above. The total amount of cells was $3.8 \times 10^8$ cells. In order to obtain the desired number of cells of 2×106 cells, the cells were resuspended in 47.5 ml of the above mentioned medium in 4 flasks. After the incubation time of 24 hours, the cells were centrifuged and washed two times with phosphate buffer in absence of $Ca^{2+}$ and $Mg^{2+}$ (Biochrom AG).

The isolation of the total RNA is performed by means of NucleoSpin RNA L Kits (Machery&Nagel) according to the manufacturer's instructions. The above described process was repeated until the necessary number of cells was obtained. This was necessary to obtain the necessary amount of 6 mg total RNA corresponding to an efficiency of 600 µg RNA per 108 cells.

Reverse Transcription/Labelling/Hybridisation

After drawing whole blood, the total RNA of the samples was isolated and tested for quality using the PAXGene Blood RNA kit (PreAnalytiX) according to the manufacturer's instructions. 10 µg total RNA were aliquoted from each sample and transcribed with 10 µg total RNA from SIGM5 cells as reference RNA to complementary DNA (cDNA) by means of the reverse transcriptase Superscript II (Invitrogen). Subsequently, the RNA is removed from the mixture by alkaline hydrolysis. In the reaction mixture a part of the dTTP was replaced by aminoallyl-dUTP (AA-dUTP) in order to render the linkage of the fluorescent dye to the cDNA possible at a later point of time.

After the purification of the reaction mixture, the cDNA of the samples and the controls were covalently labelled with the fluorescent dyes Alexa 647 and Alexa 555 and hybridised on a microarray of the SIRS-Lab company. On the microarray used, 5308 different polynucleotides with lengths of 55 to 70 base pairs were immobilised. Each of the polynucleotides represents a human gene. Additionally, there were control spots for quality assurance. One microarray is divided into 28 subarrays, each of the subarrays being arranged in a grid of 15×15 spots.

The hybridisation and the subsequent washing and drying, respectively, were carried out using the hybridisation station HS 400 (Tecon) according to the manufacturer's instructions for 10.5 hours at 42° C. The hybridisation solution used was composed of the cDNA samples, each labelled, 3.5×SSC (1×SSC comprises 150 mM NaCl and 15 mM sodiumcitrate), 0.3% sodium lauryl sulfate (v/v) 25% formamide (v/v) and each 0.8 µg µl-1 cot-1 DNA, yeast t-RNA and poly-A RNA. The subsequent washing of the microarrays was carried out at ambient temperature according to the following scheme: Rinse 90 seconds with washing buffer 1 (2×SSC, 0.03% sodium lauryl sulfate), with washing buffer 2 (1×SSC) and finally with washing buffer 3 (0.2×SSC). Subsequently, the microarrays were dried under a nitrogen flow at a pressure of 2.5 bar for more than 150 seconds at 30° C.

The hybridisation signals of the processed microarrays were subsequently read by means of the GenePix 4000B (Axon) scanner and the expression ratios of the different expressed genes were determined by means of the GenePix Pro 4.0 (Axon) software.

Evaluation:

For the analysis, the average intensity of one spot was determined as median value of the corresponding spot pixel.

Correction of Systemic Errors:

Systematic errors were corrected according to the approach of Huber et al. (2002). According to this approach, the additive and the multiplicative bias in a microarray was estimated on the basis of 70% of the gene samples present. For all further computations, the signal was transformed by means of arcus sinus hyperbolicus.

For the analysis, the normalised and transformed relative ratios of the signals of the patients samples were calculated with respect to the control. This means that the calculation for the gene no. j of the patient no. n revealed the data $G_{j,n} = \text{arcsinh}(S_{Cy5 j,n}) - \text{arcsinh}(S_{Cy3 j,n})$, wherein $[S_{Cy3 j,n}, S_{Cy5 j,n}]$ is the associated signal pair. When a spot could not be analysed for a patient (e.g. scanned picture is stained), the associated value was marked as "missing value".

Statistical Comparison:

For comparison the paired random student test was employed per gene. Both random samples contained the values of the patient groups of non-infectious MOF and infectious MOF, respectively. For choosing the differentially expressed genes, the associated p-value and the number of missing values were evaluated. It applied for the group of the selected genes that the associated p-value was smaller than 0.05.

The criterion for the grading of the examined genes was the level of the expression ratio of each gene. The most overexpressed or underexpressed genes, respectively, in the patients suffering from non-infectious MOF compared to patients suffering from infectious MOF were the interesting ones.

Table 2 shows that 721 genes of the patient sample were found, which were significantly overexpressed in the patients with infectious MOF, if compared with patients with non-infectious MOF. Furthermore, Table 3 shows that 576 genes of the patients with infectious MOF were significantly underexpressed, if compared with patients with non-infectious MOF. From the results it is clear that the gene activities listed in Table 2 and Table 3 distinguish between non-infectious causes of multiple organ failure and infectious causes of multiple organ failure. Thus, the listed gene activities provide markers for the differentiation between non-infectious and infectious causes of multiple organ failure.

TABLE 2

Significantly elevated gene activities in samples of patients with infectious MOF, if compared with the gene activities of patients with non-infectious MOF.

| | | Mean normalised and transformed expression value | | Standard deviation | | |
|---|---|---|---|---|---|---|
| GenBank Accession No. | p-value | Group of patients with non-infectious MOF | Group of patients with infectious MOF | Group of patients with non-infectious MOF | Group of patients with infectious MOF | SEQUENCE-ID |
| N32857 | 0.00 | −2.99 | 0.20 | 1.42 | 2.78 | 1 |
| N32853 | 0.00 | −0.85 | 1.60 | 2.15 | 2.89 | 2 |
| N32495 | 0.00 | −2.38 | −0.56 | 1.37 | 0.40 | 3 |
| AI701077 | 0.01 | −0.33 | 1.46 | 0.17 | 3.08 | 4 |
| M87790 | 0.00 | 1.18 | 2.93 | 1.13 | 1.24 | 5 |
| AI559317 | 0.01 | 0.20 | 1.83 | 0.54 | 2.60 | 6 |
| N34897 | 0.00 | −2.60 | −1.05 | 1.61 | 0.54 | 7 |
| AA907084 | 0.02 | 0.53 | 1.94 | 0.49 | 2.58 | 8 |
| N45223 | 0.00 | −2.88 | −1.54 | 1.24 | 0.57 | 9 |
| H70430 | 0.03 | 0.12 | 1.42 | 0.70 | 2.73 | 10 |
| R59591 | 0.01 | −0.25 | 0.97 | 0.20 | 2.06 | 11 |
| N47688 | 0.00 | −2.47 | −1.27 | 0.94 | 0.44 | 12 |
| N52930 | 0.00 | −1.49 | −0.30 | 1.06 | 0.76 | 13 |
| XM_004256 | 0.00 | −3.10 | −1.94 | 0.62 | 1.43 | 14 |
| AJ010446 | 0.00 | −0.22 | 0.93 | 0.66 | 1.11 | 15 |
| N35225 | 0.00 | −2.81 | −1.75 | 1.21 | 0.52 | 16 |
| N50680 | 0.00 | −1.30 | −0.29 | 1.58 | 0.46 | 17 |
| BC018761 | 0.00 | 1.04 | 2.02 | 0.80 | 1.27 | 18 |
| XM_009475 | 0.00 | −2.54 | −1.58 | 0.83 | 0.91 | 19 |
| N53369 | 0.04 | −0.37 | 0.55 | 1.62 | 1.39 | 20 |
| AI420863 | 0.05 | −0.17 | 0.74 | 0.47 | 1.99 | 21 |
| N33423 | 0.05 | −0.32 | 0.58 | 1.64 | 1.51 | 22 |
| AA843281 | 0.05 | 0.27 | 1.15 | 0.54 | 1.88 | 23 |
| X64641 | 0.02 | 0.26 | 1.11 | 1.09 | 1.23 | 24 |
| N52545 | 0.00 | −1.10 | −0.28 | 1.02 | 0.55 | 25 |
| X57817 | 0.01 | 0.19 | 1.00 | 0.58 | 1.21 | 26 |
| N58236 | 0.00 | −0.68 | 0.14 | 0.85 | 0.56 | 27 |
| XM_056556 | 0.00 | −3.12 | −2.31 | 0.58 | 0.99 | 28 |
| N59170 | 0.01 | −0.22 | 0.59 | 1.35 | 0.74 | 29 |
| N58392 | 0.00 | −0.85 | −0.04 | 0.71 | 0.62 | 30 |
| N34672 | 0.02 | −0.54 | 0.26 | 1.74 | 0.39 | 31 |
| XM_015396 | 0.00 | −0.27 | 0.52 | 0.68 | 0.81 | 32 |
| X05875 | 0.01 | −2.86 | −2.09 | 0.55 | 1.15 | 33 |
| N48715 | 0.00 | −1.12 | −0.36 | 0.70 | 0.61 | 34 |
| N90140 | 0.05 | −0.44 | 0.32 | 0.29 | 1.71 | 35 |
| NM_002415 | 0.00 | −1.66 | −0.90 | 0.63 | 0.56 | 36 |
| AI890242 | 0.00 | −0.14 | 0.59 | 0.25 | 0.72 | 37 |
| AI589096 | 0.00 | −0.39 | 0.32 | 0.56 | 0.54 | 38 |
| NM_001911 | 0.04 | −2.61 | −1.91 | 0.77 | 1.44 | 39 |
| N39242 | 0.05 | −0.56 | 0.12 | 1.75 | 0.52 | 40 |
| N35493 | 0.04 | −0.45 | 0.23 | 1.69 | 0.46 | 41 |
| AI271764 | 0.00 | −0.66 | −0.02 | 0.70 | 0.62 | 42 |
| NM_006936 | 0.00 | −2.00 | −1.37 | 0.46 | 0.55 | 43 |
| NM_005225 | 0.00 | −0.90 | −0.26 | 0.58 | 0.53 | 44 |
| R98960 | 0.04 | −0.37 | 0.26 | 1.41 | 0.70 | 45 |
| NM_000714.3 | 0.00 | 0.48 | 1.11 | 0.44 | 0.88 | 46 |
| N48180 | 0.01 | −1.08 | −0.45 | 1.05 | 0.45 | 47 |
| NM_002295 | 0.02 | −3.17 | −2.56 | 0.44 | 1.09 | 48 |
| AI697365 | 0.01 | 0.62 | 1.22 | 0.82 | 0.67 | 49 |
| NM_001404 | 0.00 | −2.56 | −1.96 | 0.38 | 0.86 | 50 |

TABLE 2-continued

Significantly elevated gene activities in samples of patients with infectious MOF, if compared with the gene activities of patients with non-infectious MOF.

| GenBank Accession No. | p-value | Mean normalised and transformed expression value | | Standard deviation | | SEQUENCE-ID |
|---|---|---|---|---|---|---|
| | | Group of patients with non-infectious MOF | Group of patients with infectious MOF | Group of patients with non-infectious MOF | Group of patients with infectious MOF | |
| NM_176800.1 | 0.00 | −0.31 | 0.29 | 0.51 | 0.42 | 51 |
| XM_027885 | 0.03 | −3.23 | −2.63 | 0.37 | 1.17 | 52 |
| NM_006597.3 | 0.00 | −2.42 | −1.84 | 0.50 | 0.79 | 53 |
| NM_002211 | 0.00 | −1.59 | −1.02 | 0.68 | 0.54 | 54 |
| NM_001570 | 0.00 | −0.55 | 0.03 | 0.53 | 0.49 | 55 |
| AI888606 | 0.03 | −0.16 | 0.40 | 0.44 | 1.11 | 56 |
| NM_006636.2 | 0.04 | −3.49 | −2.93 | 0.53 | 1.16 | 57 |
| AA458827 | 0.00 | 0.15 | 0.71 | 0.33 | 0.60 | 58 |
| AA398757 | 0.01 | 0.11 | 0.67 | 0.57 | 0.81 | 59 |
| NM_000814.2 | 0.00 | −0.07 | 0.49 | 0.48 | 0.75 | 60 |
| NM_000963 | 0.00 | −0.41 | 0.15 | 0.86 | 0.33 | 61 |
| AI913322 | 0.02 | −0.68 | −0.14 | 0.68 | 0.92 | 62 |
| N20922 | 0.04 | −0.72 | −0.17 | 1.27 | 0.51 | 63 |
| R49085 | 0.00 | 0.02 | 0.57 | 0.64 | 0.56 | 64 |
| N54935 | 0.01 | −0.74 | −0.19 | 0.97 | 0.38 | 65 |
| XM_027358 | 0.01 | −1.49 | −0.95 | 0.75 | 0.59 | 66 |
| NM_031200 | 0.00 | 0.11 | 0.65 | 0.57 | 0.57 | 67 |
| AA805531 | 0.00 | −0.07 | 0.47 | 0.33 | 0.53 | 68 |
| NM_000194 | 0.04 | −2.64 | −2.12 | 0.70 | 1.02 | 69 |
| AI623567 | 0.01 | 0.39 | 0.92 | 0.59 | 0.73 | 70 |
| N64495 | 0.00 | −0.49 | 0.02 | 0.63 | 0.37 | 71 |
| NM_002156 | 0.01 | −2.26 | −1.75 | 0.59 | 0.70 | 72 |
| NM_012068 | 0.00 | −1.40 | −0.89 | 0.54 | 0.40 | 73 |
| R43722 | 0.02 | −0.45 | 0.05 | 0.65 | 0.80 | 74 |
| NM_001686 | 0.03 | −2.63 | −2.13 | 0.32 | 0.93 | 75 |
| NM_002969 | 0.00 | −0.92 | −0.42 | 0.46 | 0.53 | 76 |
| NM_003295 | 0.04 | −2.72 | −2.24 | 0.45 | 0.98 | 77 |
| XM_039372 | 0.02 | −2.43 | −1.95 | 0.26 | 0.92 | 78 |
| AA731679 | 0.02 | 0.17 | 0.65 | 0.79 | 0.61 | 79 |
| AA620762 | 0.00 | −0.04 | 0.44 | 0.21 | 0.50 | 80 |
| AI499889 | 0.01 | −0.01 | 0.47 | 0.67 | −0.64 | 81 |
| N33530 | 0.00 | −0.30 | 0.18 | 0.70 | 0.31 | 82 |
| NM_002033 | 0.00 | −1.92 | −1.44 | 0.39 | 0.63 | 83 |
| AA436651 | 0.00 | −0.26 | 0.21 | 0.54 | 0.26 | 84 |
| NM_001540 | 0.00 | −1.42 | −0.95 | 0.42 | 0.54 | 85 |
| NM_004257 | 0.00 | −0.85 | −0.38 | 0.33 | 0.25 | 86 |
| NM_014280.1 | 0.00 | −1.45 | −0.98 | 0.58 | 0.47 | 87 |
| NM_000930.2 | 0.00 | −1.30 | −0.83 | 0.64 | 0.51 | 88 |
| XM_002101 | 0.00 | −0.63 | −0.17 | 0.63 | 0.27 | 89 |
| AI733269 | 0.00 | −0.18 | 0.29 | 0.45 | 0.36 | 90 |
| NM_001168 | 0.02 | −2.14 | −1.67 | 0.61 | 0.77 | 91 |
| XM_052636 | 0.00 | −1.51 | −1.04 | 0.35 | 0.48 | 92 |
| AI689318 | 0.00 | −1.00 | −0.54 | 0.55 | 0.46 | 93 |
| NM_001212 | 0.01 | −1.65 | −1.19 | 0.56 | 0.64 | 94 |
| R37251 | 0.00 | 0.61 | 1.06 | 0.39 | 0.63 | 95 |
| NM_001166 | 0.00 | −0.76 | −0.31 | 0.53 | 0.41 | 96 |
| XM_056798 | 0.01 | −1.34 | −0.89 | 0.66 | 0.51 | 97 |
| NM_005052 | 0.01 | 0.41 | 0.86 | 0.37 | 0.67 | 98 |
| NM_003379 | 0.00 | −1.45 | −1.00 | 0.41 | 0.51 | 99 |
| XM_048068 | 0.00 | −0.37 | 0.08 | 0.43 | 0.42 | 100 |
| NM_000577 | 0.01 | 0.45 | 0.90 | 0.32 | 0.67 | 101 |
| NM_001101 | 0.00 | −0.69 | −0.25 | 0.43 | 0.58 | 102 |
| D31890 | 0.01 | −1.79 | −1.36 | 0.56 | 0.55 | 103 |
| N49976 | 0.03 | −0.26 | 0.17 | 0.90 | 0.50 | 104 |
| XM_008679 | 0.01 | −0.85 | −0.41 | 0.57 | 0.56 | 105 |
| N33187 | 0.01 | −0.06 | 0.38 | 0.52 | 0.54 | 106 |
| R42782 | 0.00 | −0.09 | 0.34 | 0.36 | 0.45 | 107 |
| N49751 | 0.01 | 0.71 | 1.14 | 0.48 | 0.64 | 108 |
| AI910456 | 0.04 | −1.12 | −0.69 | 0.73 | 0.75 | 109 |
| NM_001569 | 0.00 | −1.10 | −0.67 | 0.38 | 0.46 | 110 |
| H90322 | 0.00 | 0.05 | 0.48 | 0.27 | 0.51 | 111 |
| AI926659 | 0.00 | 0.05 | 0.48 | 0.37 | 0.44 | 112 |
| XM_047499 | 0.01 | −1.29 | −0.86 | 0.46 | 0.67 | 113 |
| AA437224 | 0.00 | −0.71 | −0.28 | 0.46 | 0.24 | 114 |
| NM_021798 | 0.00 | −0.32 | 0.11 | 0.44 | 0.36 | 115 |
| NM_000584 | 0.02 | −1.82 | −1.40 | 0.61 | 0.64 | 116 |
| AA452122 | 0.00 | −0.40 | 0.02 | 0.60 | 0.41 | 117 |
| NM_002189 | 0.01 | 0.10 | 0.52 | 0.48 | 0.57 | 118 |

TABLE 2-continued

Significantly elevated gene activities in samples of patients with infectious MOF, if compared with the gene activities of patients with non-infectious MOF.

| GenBank Accession No. | p-value | Mean normalised and transformed expression value | | Standard deviation | | SEQUENCE-ID |
|---|---|---|---|---|---|---|
| | | Group of patients with non-infectious MOF | Group of patients with infectious MOF | Group of patients with non-infectious MOF | Group of patients with infectious MOF | |
| AA001367 | 0.00 | −0.13 | 0.29 | 0.37 | 0.57 | 119 |
| AI129679 | 0.00 | −1.27 | −0.85 | 0.31 | 0.37 | 120 |
| D26599 | 0.01 | −1.90 | −1.48 | 0.50 | 0.58 | 121 |
| NM_170665.2 | 0.00 | −1.19 | −0.78 | 0.49 | 0.45 | 122 |
| NM_006419 | 0.00 | −0.16 | 0.25 | 0.39 | 0.51 | 123 |
| W85706 | 0.00 | −1.07 | −0.66 | 0.30 | 0.37 | 124 |
| AA897528 | 0.00 | −0.50 | −0.09 | 0.65 | 0.30 | 125 |
| NM_003358 | 0.04 | 0.56 | 0.97 | 0.50 | 0.82 | 126 |
| N35251 | 0.00 | −0.18 | 0.22 | 0.52 | 0.41 | 127 |
| NM_004863 | 0.00 | −0.63 | −0.22 | 0.37 | 0.48 | 128 |
| NM_001950 | 0.00 | −0.82 | −0.41 | 0.40 | 0.33 | 129 |
| NM_006260 | 0.03 | −0.63 | −0.22 | 0.61 | 0.67 | 130 |
| NM_170708 | 0.03 | −1.52 | −1.12 | 0.54 | 0.63 | 131 |
| N63024 | 0.01 | 0.64 | 1.04 | 0.43 | 0.56 | 132 |
| NM_017595 | 0.00 | −0.85 | −0.45 | 0.36 | 0.33 | 133 |
| AI364529 | 0.02 | −0.97 | −0.57 | 0.59 | 0.59 | 134 |
| NM_013432 | 0.00 | −0.30 | 0.10 | 0.31 | 0.28 | 135 |
| NM_006736.2 | 0.00 | −0.56 | −0.16 | 0.24 | 0.37 | 136 |
| NM_002128 | 0.02 | −1.84 | −1.44 | 0.40 | 0.69 | 137 |
| AA441793 | 0.00 | −0.70 | −0.31 | 0.45 | 0.33 | 138 |
| N76019 | 0.00 | −0.27 | 0.13 | 0.35 | 0.30 | 139 |
| XM_048665 | 0.00 | −0.28 | 0.11 | 0.38 | 0.35 | 140 |
| NM_003467 | 0.01 | −1.80 | −1.41 | 0.32 | 0.62 | 141 |
| N59330 | 0.01 | −0.21 | 0.19 | 0.56 | 0.50 | 142 |
| NM_004672 | 0.00 | −0.08 | 0.32 | 0.44 | 0.26 | 143 |
| AA426021 | 0.01 | 0.06 | 0.45 | 0.28 | 0.61 | 144 |
| XM_008608 | 0.00 | −0.60 | −0.21 | 0.54 | 0.34 | 145 |
| H44908 | 0.00 | −0.55 | −0.16 | 0.42 | 0.33 | 146 |
| AA699412 | 0.00 | −0.47 | −0.08 | 0.48 | 0.35 | 147 |
| AI572080 | 0.01 | 0.28 | 0.67 | 0.41 | 0.52 | 148 |
| NM_012072 | 0.02 | −1.86 | −1.47 | 0.47 | 0.63 | 149 |
| XM_035638 | 0.04 | −1.96 | −1.57 | 0.40 | 0.80 | 150 |
| BC001604 | 0.00 | −1.13 | −0.74 | 0.40 | 0.33 | 151 |
| AA481282 | 0.00 | −0.11 | 0.27 | 0.54 | 0.40 | 152 |
| NM_003376 | 0.01 | −1.17 | −0.78 | 0.54 | 0.42 | 153 |
| H11661 | 0.00 | −0.07 | 0.32 | 0.25 | 0.37 | 154 |
| AI435179 | 0.01 | −0.08 | 0.30 | 0.68 | 0.37 | 155 |
| XM_006800 | 0.01 | 0.19 | 0.57 | 0.38 | 0.55 | 156 |
| NM_000397.2 | 0.00 | −0.56 | −0.17 | 0.37 | 0.28 | 157 |
| AA424023 | 0.02 | 0.01 | 0.39 | 0.43 | 0.63 | 158 |
| XM_012949 | 0.02 | −1.81 | −1.43 | 0.45 | 0.64 | 159 |
| W84866 | 0.00 | 0.14 | 0.52 | 0.44 | 0.45 | 160 |
| N62672 | 0.01 | −0.21 | 0.17 | 0.60 | 0.44 | 161 |
| NM_001530 | 0.01 | −0.16 | 0.21 | 0.25 | 0.62 | 162 |
| NM_002157.1 | 0.03 | −2.21 | −1.83 | 0.43 | 0.71 | 163 |
| NM_003258 | 0.02 | −1.80 | −1.43 | 0.68 | 0.46 | 164 |
| AI863135 | 0.04 | 0.87 | 1.25 | 0.40 | 0.76 | 165 |
| NM_004083 | 0.01 | −0.95 | −0.58 | 0.46 | 0.47 | 166 |
| H06194 | 0.00 | −0.92 | −0.54 | 0.45 | 0.30 | 167 |
| XM_047570 | 0.03 | −1.61 | −1.24 | 0.41 | 0.68 | 168 |
| D26598 | 0.01 | −1.23 | −0.86 | 0.27 | 0.57 | 169 |
| R44955 | 0.01 | −0.08 | 0.29 | 0.55 | 0.49 | 170 |
| NM_012297 | 0.02 | −1.60 | −1.22 | 0.48 | 0.59 | 171 |
| T84080 | 0.02 | 0.13 | 0.49 | 0.57 | 0.52 | 172 |
| H52810 | 0.00 | 0.13 | 0.50 | 0.33 | 0.44 | 173 |
| XM_055188 | 0.04 | 0.94 | 1.30 | 0.36 | 0.75 | 174 |
| AI184987 | 0.01 | 0.19 | 0.56 | 0.51 | 0.50 | 175 |
| AI733177 | 0.02 | 0.54 | 0.90 | 0.41 | 0.63 | 176 |
| NM_006016 | 0.02 | −1.15 | −0.78 | 0.44 | 0.60 | 177 |
| XM_006867 | 0.02 | 0.09 | 0.46 | 0.33 | 0.62 | 178 |
| NM_004475.1 | 0.02 | 0.95 | 1.32 | 0.40 | 0.60 | 179 |
| AA485242 | 0.03 | 0.34 | 0.70 | 0.49 | 0.62 | 180 |
| NM_003300 | 0.01 | −1.49 | −1.13 | 0.31 | 0.54 | 181 |
| NM_032957 | 0.00 | −0.88 | −0.52 | 0.32 | 0.39 | 182 |
| XM_033862 | 0.00 | −0.01 | 0.35 | 0.29 | 0.36 | 183 |
| W80385 | 0.01 | 0.10 | 0.46 | 0.36 | 0.52 | 184 |
| H99099 | 0.01 | −0.04 | 0.32 | 0.37 | 0.52 | 185 |
| N67859 | 0.00 | −0.77 | −0.41 | 0.34 | 0.39 | 186 |

TABLE 2-continued

Significantly elevated gene activities in samples of patients with infectious MOF, if compared with the gene activities of patients with non-infectious MOF.

| GenBank Accession No. | p-value | Mean normalised and transformed expression value | | Standard deviation | | SEQUENCE-ID |
|---|---|---|---|---|---|---|
| | | Group of patients with non-infectious MOF | Group of patients with infectious MOF | Group of patients with non-infectious MOF | Group of patients with infectious MOF | |
| NM_001013 | 0.04 | −1.88 | −1.52 | 0.44 | 0.68 | 187 |
| NM_006641 | 0.02 | −0.36 | 0.00 | 0.69 | 0.35 | 188 |
| N70546 | 0.00 | −0.11 | 0.25 | 0.38 | 0.40 | 189 |
| XM_015278 | 0.00 | −0.36 | −0.01 | 0.33 | 0.42 | 190 |
| AI932670 | 0.00 | −0.15 | 0.20 | 0.36 | 0.43 | 191 |
| NM_175617 | 0.00 | −0.11 | 0.25 | 0.29 | 0.26 | 192 |
| NM_004377.2 | 0.02 | −0.88 | −0.53 | 0.52 | 0.50 | 193 |
| NM_003153 | 0.00 | −0.39 | −0.04 | 0.30 | 0.48 | 194 |
| AI910804 | 0.03 | −0.65 | −0.30 | 0.51 | 0.57 | 195 |
| AI221860 | 0.00 | −0.30 | 0.05 | 0.17 | 0.43 | 196 |
| AI866414 | 0.00 | −0.37 | −0.02 | 0.33 | 0.27 | 197 |
| BC020968 | 0.03 | −1.77 | −1.42 | 0.36 | 0.65 | 198 |
| AA484213 | 0.05 | −0.49 | −0.14 | 0.90 | 0.27 | 199 |
| XM_003593 | 0.00 | −0.52 | −0.17 | 0.44 | 0.27 | 200 |
| XM_008738 | 0.02 | −1.46 | −1.11 | 0.54 | 0.49 | 201 |
| NM_032964 | 0.00 | −0.48 | −0.13 | 0.41 | 0.20 | 202 |
| NM_001455 | 0.00 | 0.26 | 0.61 | 0.42 | 0.41 | 203 |
| NM_002994 | 0.00 | −0.61 | −0.26 | 0.35 | 0.43 | 204 |
| NM_004222 | 0.00 | −1.44 | −1.10 | 0.30 | 0.45 | 205 |
| H48923 | 0.00 | −0.59 | −0.25 | 0.35 | 0.39 | 206 |
| T47430 | 0.05 | 0.41 | 0.75 | 0.38 | 0.71 | 207 |
| NM_032963 | 0.00 | −0.45 | −0.11 | 0.52 | 0.22 | 208 |
| XM_045933 | 0.00 | 0.22 | 0.56 | 0.23 | −0.41 | 209 |
| T99746 | 0.03 | 0.26 | 0.60 | 0.49 | 0.52 | 210 |
| XM_012039 | 0.01 | −1.44 | −1.10 | 0.44 | 0.43 | 211 |
| NM_004740 | 0.00 | −0.46 | −0.12 | 0.29 | 0.24 | 212 |
| NM_001681.2 | 0.05 | −1.39 | −0.05 | 0.61 | 0.60 | 213 |
| AI027259 | 0.00 | −0.40 | −0.06 | 0.49 | 0.28 | 214 |
| AA431552 | 0.00 | −0.63 | −0.30 | 0.41 | 0.32 | 215 |
| NM_000029 | 0.00 | 0.30 | 0.63 | 0.32 | 0.42 | 216 |
| XM_041847 | 0.05 | −1.02 | −0.68 | 0.69 | 0.51 | 217 |
| NM_005920 | 0.00 | −0.90 | −0.56 | 0.28 | 0.33 | 218 |
| NM_002394 | 0.01 | −1.03 | −0.69 | 0.49 | 0.39 | 219 |
| AI093704 | 0.01 | −0.32 | 0.02 | 0.35 | 0.47 | 220 |
| XM_043359 | 0.01 | 0.21 | 0.55 | 0.36 | 0.51 | 221 |
| H48445 | 0.01 | 0.28 | 0.61 | 0.38 | 0.53 | 222 |
| XM_015815 | 0.02 | −1.13 | −0.80 | 0.52 | 0.50 | 223 |
| NM_001774 | 0.00 | −0.07 | 0.27 | 0.31 | 0.42 | 224 |
| AI937053 | 0.00 | −0.42 | −0.09 | 0.39 | 0.26 | 225 |
| AA493719 | 0.01 | −0.61 | −0.28 | 0.52 | 0.35 | 226 |
| NM_002996 | 0.01 | 0.19 | 0.51 | 0.33 | 0.44 | 227 |
| AI025039 | 0.01 | 0.16 | 0.49 | 0.31 | 0.47 | 228 |
| NM_139049 | 0.02 | −0.52 | −0.19 | 0.60 | 0.34 | 229 |
| NM_006238.2 | 0.00 | −0.29 | 0.04 | 0.21 | 0.26 | 230 |
| XM_031456 | 0.00 | −0.67 | −0.35 | 0.30 | 0.30 | 231 |
| AA455096 | 0.00 | −0.29 | 0.03 | 0.29 | 0.32 | 232 |
| XM_047675 | 0.03 | 0.36 | 0.68 | 0.26 | 0.65 | 233 |
| AI809252 | 0.00 | −0.14 | 0.18 | 0.36 | 0.34 | 234 |
| NM_139047 | 0.00 | −0.45 | −0.13 | 0.47 | 0.31 | 235 |
| AI760793 | 0.01 | −0.47 | −0.15 | 0.47 | 0.33 | 236 |
| NM_000204 | 0.00 | −0.03 | 0.29 | 0.25 | 0.40 | 237 |
| AI860121 | 0.01 | 0.55 | 0.87 | 0.37 | 0.48 | 238 |
| H50222 | 0.00 | −0.13 | 0.19 | 0.19 | 0.34 | 239 |
| XM_041101 | 0.02 | −1.06 | −0.74 | 0.34 | 0.56 | 240 |
| XM_035854 | 0.01 | 0.09 | 0.41 | 0.47 | 0.44 | 241 |
| AA043903 | 0.01 | −0.73 | −0.41 | 0.52 | 0.31 | 242 |
| R40406 | 0.03 | −0.89 | −0.58 | 0.48 | 0.52 | 243 |
| N98510 | 0.04 | −1.22 | −0.90 | 0.51 | 0.56 | 244 |
| H05449 | 0.03 | −0.15 | 0.16 | 0.52 | 0.50 | 245 |
| AI567338 | 0.01 | −0.11 | 0.20 | 0.43 | 0.39 | 246 |
| NM_000308.1 | 0.00 | −0.19 | 0.13 | 0.29 | 0.42 | 247 |
| R40880 | 0.00 | −0.21 | 0.11 | 0.40 | 0.34 | 248 |
| H52284 | 0.00 | −0.26 | 0.05 | 0.41 | 0.27 | 249 |
| NM_030662 | 0.00 | −0.47 | −0.16 | 0.22 | 0.27 | 250 |
| NM_032965 | 0.02 | 0.52 | 0.83 | 0.41 | 0.47 | 251 |
| NM_004322 | 0.00 | −0.34 | −0.03 | 0.32 | 0.27 | 252 |
| XM_002762 | 0.00 | −0.52 | −0.21 | 0.22 | 0.25 | 253 |
| AI679230 | 0.00 | −0.40 | −0.09 | 0.43 | 0.33 | 254 |

TABLE 2-continued

Significantly elevated gene activities in samples of patients with infectious MOF, if compared with the gene activities of patients with non-infectious MOF.

| GenBank Accession No. | p-value | Mean normalised and transformed expression value | | Standard deviation | | SEQUENCE-ID |
|---|---|---|---|---|---|---|
| | | Group of patients with non-infectious MOF | Group of patients with infectious MOF | Group of patients with non-infectious MOF | Group of patients with infectious MOF | |
| AI368670 | 0.00 | −0.23 | 0.08 | 0.30 | 0.31 | 255 |
| NM_006415 | 0.01 | −0.71 | −0.40 | 0.45 | 0.33 | 256 |
| NM_004379 | 0.00 | −0.54 | −0.23 | 0.24 | 0.24 | 257 |
| NM_002974 | 0.02 | 0.02 | 0.33 | 0.49 | 0.38 | 258 |
| AI914729 | 0.02 | −0.11 | 0.20 | 0.51 | 0.40 | 259 |
| NM_032989 | 0.00 | −0.17 | 0.14 | 0.23 | 0.28 | 260 |
| AI799645 | 0.04 | 0.14 | 0.45 | 0.39 | 0.61 | 261 |
| AA436553 | 0.01 | −0.33 | −0.03 | 0.59 | 0.24 | 262 |
| NM_033015 | 0.00 | −0.37 | −0.06 | 0.32 | 0.25 | 263 |
| XM_002224 | 0.01 | −0.26 | 0.04 | 0.57 | 0.28 | 264 |
| AI708030 | 0.00 | 0.11 | 0.41 | 0.37 | 0.32 | 265 |
| AI041544 | 0.00 | −0.28 | 0.02 | 0.28 | 0.27 | 266 |
| NM_005801 | 0.03 | −1.39 | −1.09 | 0.36 | 0.54 | 267 |
| NM_022559 | 0.00 | −0.63 | −0.33 | 0.42 | 0.24 | 268 |
| XM_043864 | 0.00 | −0.40 | −0.10 | 0.32 | 0.31 | 269 |
| NM_003840 | 0.01 | −0.42 | −0.12 | 0.52 | 0.25 | 270 |
| AI565083 | 0.00 | −0.28 | 0.02 | 0.32 | 0.24 | 271 |
| R91168 | 0.01 | 0.15 | 0.45 | 0.36 | 0.40 | 272 |
| AI799787 | 0.01 | 0.12 | 0.41 | 0.34 | 0.38 | 273 |
| AI652564 | 0.00 | −0.91 | −0.61 | 0.31 | 0.30 | 274 |
| H05310 | 0.00 | 0.02 | 0.32 | 0.30 | 0.29 | 275 |
| AA708806 | 0.00 | −0.22 | 0.08 | 0.24 | 0.26 | 276 |
| H74205 | 0.03 | 0.07 | 0.37 | 0.42 | 0.49 | 277 |
| NM_000061 | 0.03 | −1.59 | −1.30 | 0.40 | 0.53 | 278 |
| NM_003110.3 | 0.00 | −0.29 | 0.00 | 0.38 | 0.27 | 279 |
| AA625887 | 0.00 | −0.30 | −0.01 | 0.22 | 0.23 | 280 |
| H41124 | 0.03 | −0.37 | −0.08 | 0.39 | 0.48 | 281 |
| AI769514 | 0.02 | −0.58 | −0.28 | 0.56 | 0.35 | 282 |
| XM_036107 | 0.03 | −0.27 | 0.02 | 0.27 | 0.53 | 283 |
| R52679 | 0.01 | −1.03 | −0.74 | 0.36 | 0.35 | 284 |
| AI217811 | 0.04 | 0.02 | 0.31 | 0.31 | 0.59 | 285 |
| NM_004168 | 0.02 | −0.63 | −0.34 | 0.42 | 0.44 | 286 |
| AI933607 | 0.03 | −0.24 | 0.05 | 0.32 | 0.55 | 287 |
| NM_007052.3 | 0.03 | −0.24 | 0.05 | 0.61 | 0.29 | 288 |
| AI799137 | 0.02 | −0.42 | −0.12 | 0.52 | 0.37 | 289 |
| NM_002720 | 0.00 | −0.64 | −0.35 | 0.28 | 0.34 | 290 |
| R26635 | 0.04 | −0.16 | 0.13 | 0.32 | 0.57 | 291 |
| AI625594 | 0.00 | −0.01 | 0.28 | 0.29 | 0.31 | 292 |
| NM_001562 | 0.00 | −0.42 | −0.13 | 0.22 | 0.27 | 293 |
| W93717 | 0.05 | 0.11 | 0.40 | 0.64 | 0.40 | 294 |
| NM_002521.1 | 0.01 | −0.10 | 0.19 | 0.44 | 0.29 | 295 |
| R42543 | 0.05 | 0.26 | 0.55 | 0.45 | 0.54 | 296 |
| AI302949 | 0.00 | −0.13 | 0.16 | 0.21 | 0.23 | 297 |
| H54279 | 0.00 | −0.01 | 0.27 | 0.29 | 0.32 | 298 |
| AI219513 | 0.00 | −0.47 | −0.19 | 0.41 | 0.27 | 299 |
| N68173 | 0.00 | −0.11 | 0.18 | 0.26 | 0.38 | 300 |
| AA496235 | 0.00 | −0.38 | −0.09 | 0.41 | 0.28 | 301 |
| AI742529 | 0.03 | 0.39 | 0.67 | 0.33 | 0.51 | 302 |
| H79534 | 0.01 | −0.50 | −0.21 | 0.47 | 0.32 | 303 |
| AA002267 | 0.03 | −0.04 | 0.25 | 0.36 | 0.47 | 304 |
| H52638 | 0.00 | −0.38 | −0.10 | 0.40 | 0.28 | 305 |
| N70324 | 0.01 | 0.07 | 0.35 | 0.47 | 0.33 | 306 |
| NM_003805 | 0.02 | −0.83 | −0.55 | 0.47 | 0.36 | 307 |
| N59766 | 0.03 | −0.04 | 0.24 | 0.41 | 0.43 | 308 |
| XM_034770 | 0.04 | −1.26 | −0.98 | 0.44 | 0.45 | 309 |
| AI538438 | 0.01 | 0.06 | 0.34 | 0.43 | 0.31 | 310 |
| AI250800 | 0.00 | 0.05 | 0.32 | 0.23 | 0.29 | 311 |
| AA845475 | 0.00 | −0.24 | 0.04 | 0.39 | 0.25 | 312 |
| AI700169 | 0.00 | −0.23 | 0.05 | 0.33 | 0.30 | 313 |
| NM_003639) | 0.00 | −0.37 | −0.09 | 0.26 | 0.31 | 314 |
| AI125864 | 0.03 | −0.27 | 0.01 | 0.60 | 0.24 | 315 |
| NM_000757 | 0.03 | 0.12 | 0.40 | 0.38 | 0.48 | 316 |
| NM_006216 | 0.03 | −0.12 | 0.16 | 0.45 | 0.42 | 317 |
| AI077481 | 0.04 | 0.21 | 0.49 | 0.41 | 0.48 | 318 |
| AI149647 | 0.03 | −0.13 | 0.15 | 0.43 | 0.46 | 319 |
| XM_030906 | 0.01 | 0.18 | 0.45 | 0.28 | 0.39 | 320 |
| NM_004834 | 0.00 | −0.68 | −0.41 | 0.27 | 0.35 | 321 |
| XM_031287 | 0.01 | 0.11 | 0.38 | 0.27 | 0.41 | 322 |

TABLE 2-continued

Significantly elevated gene activities in samples of patients with infectious MOF, if compared with the gene activities of patients with non-infectious MOF.

| GenBank Accession No. | p-value | Mean normalised and transformed expression value | | Standard deviation | | SEQUENCE-ID |
|---|---|---|---|---|---|---|
| | | Group of patients with non-infectious MOF | Group of patients with infectious MOF | Group of patients with non-infectious MOF | Group of patients with infectious MOF | |
| AI923251 | 0.00 | −0.25 | 0.02 | 0.20 | 0.24 | 323 |
| AI203697 | 0.00 | −0.22 | 0.05 | 0.31 | 0.18 | 324 |
| AA621192 | 0.02 | 0.04 | 0.31 | 0.34 | 0.45 | 325 |
| XM_008450 | 0.02 | −0.24 | 0.03 | 0.51 | 0.29 | 326 |
| AI540674 | 0.00 | −0.76 | −0.49 | 0.25 | 0.34 | 327 |
| AA514237 | 0.03 | 0.35 | 0.62 | 0.31 | 0.47 | 328 |
| AI348271 | 0.01 | −0.11 | 0.16 | 0.45 | 0.26 | 329 |
| NM_000684.1 | 0.02 | 0.41 | 0.68 | 0.29 | 0.44 | 330 |
| NM_001951 | 0.03 | −0.67 | −0.40 | 0.50 | 0.40 | 331 |
| N55249 | 0.01 | −0.42 | −0.15 | 0.45 | 0.31 | 332 |
| AI150732 | 0.01 | −0.20 | 0.07 | 0.34 | 0.34 | 333 |
| AI147315 | 0.03 | 0.35 | 0.62 | 0.38 | 0.45 | 334 |
| NM_003010 | 0.00 | −0.46 | −0.20 | 0.34 | 0.25 | 335 |
| AA460460 | 0.01 | −0.22 | 0.05 | 0.47 | 0.28 | 336 |
| AI651337 | 0.01 | −0.49 | −0.22 | 0.41 | 0.31 | 337 |
| AA971087 | 0.01 | −0.19 | 0.08 | 0.42 | 0.25 | 338 |
| NM_003811 | 0.03 | −1.09 | −0.82 | 0.50 | 0.37 | 339 |
| XM_053519 | 0.01 | −0.30 | −0.04 | 0.26 | 0.39 | 340 |
| NM_001609.1 | 0.00 | −0.24 | 0.03 | 0.29 | 0.29 | 341 |
| AA463423 | 0.00 | −0.17 | 0.09 | 0.22 | 0.35 | 342 |
| AA648848 | 0.02 | 0.04 | 0.30 | 0.35 | 0.42 | 343 |
| AI141692 | 0.05 | −0.12 | 0.14 | 0.67 | 0.22 | 344 |
| R79239 | 0.04 | 0.06 | 0.33 | 0.50 | 0.42 | 345 |
| AI298171 | 0.00 | −0.28 | −0.01 | 0.17 | 0.21 | 346 |
| H17432 | 0.03 | −0.29 | −0.03 | 0.57 | 0.23 | 347 |
| NM_004635 | 0.05 | −1.36 | −1.10 | 0.31 | 0.51 | 348 |
| NM_005409 | 0.02 | 0.14 | 0.40 | 0.20 | 0.50 | 349 |
| AI452845 | 0.03 | 0.23 | 0.49 | 0.37 | 0.43 | 350 |
| AI222914 | 0.00 | −0.03 | 0.23 | 0.29 | 0.24 | 351 |
| AI885492 | 0.00 | −0.06 | 0.20 | 0.34 | 0.20 | 352 |
| NM_002953 | 0.01 | −0.61 | −0.35 | 0.24 | 0.41 | 353 |
| AI201175 | 0.01 | 0.25 | 0.51 | 0.30 | 0.33 | 354 |
| NM_001735 | 0.02 | −0.45 | −0.20 | 0.47 | 0.29 | 355 |
| D78151 | 0.02 | −0.70 | −0.44 | 0.42 | 0.34 | 356 |
| NM_006712 | 0.00 | −0.20 | 0.06 | 0.36 | 0.24 | 357 |
| AF004429 | 0.00 | −0.63 | −0.37 | 0.29 | 0.29 | 358 |
| NM_031409 | 0.03 | 0.19 | 0.44 | 0.32 | 0.45 | 359 |
| AI742287 | 0.01 | −0.30 | −0.04 | 0.41 | 0.27 | 360 |
| BC015542 | 0.02 | −0.42 | −0.16 | 0.34 | 0.42 | 361 |
| AI685923 | 0.00 | −0.43 | −0.18 | 0.32 | 0.22 | 362 |
| NM_002218.1 | 0.01 | −0.55 | −0.29 | 0.34 | 0.28 | 363 |
| XM_003913 | 0.00 | −0.05 | 0.20 | 0.29 | 0.29 | 364 |
| N53480 | 0.02 | −0.64 | −0.39 | 0.40 | 0.38 | 365 |
| XM_048511 | 0.00 | −0.35 | −0.10 | 0.37 | 0.25 | 366 |
| R06710 | 0.02 | 0.05 | 0.30 | 0.39 | 0.35 | 367 |
| AI694720 | 0.01 | 0.29 | 0.54 | 0.28 | 0.34 | 368 |
| AI910988 | 0.00 | 0.07 | 0.32 | 0.23 | 0.33 | 369 |
| AA411624 | 0.02 | −0.52 | −0.27 | 0.33 | 0.38 | 370 |
| BC024270 | 0.00 | −0.43 | −0.18 | 0.32 | 0.27 | 371 |
| T90460 | 0.01 | −0.39 | −0.14 | 0.48 | 0.17 | 372 |
| NM_004850 | 0.02 | −0.92 | −0.67 | 0.41 | 0.32 | 373 |
| AA044390 | 0.03 | −0.01 | 0.24 | 0.26 | 0.45 | 374 |
| NM_005347.2 | 0.00 | −0.26 | −0.01 | 0.21 | 0.23 | 375 |
| XM_027216 | 0.03 | −0.68 | −0.43 | 0.42 | 0.39 | 376 |
| H53259 | 0.04 | 0.45 | 0.70 | 0.35 | 0.45 | 377 |
| R26717 | 0.02 | −0.02 | 0.22 | 0.40 | 0.35 | 378 |
| AI912970 | 0.02 | 0.19 | 0.44 | 0.36 | 0.35 | 379 |
| XM_001687 | 0.04 | −0.91 | −0.66 | 0.44 | 0.40 | 380 |
| NM_000565 | 0.04 | −0.67 | −0.43 | 0.27 | 0.50 | 381 |
| AI374990 | 0.01 | −0.14 | 0.10 | 0.31 | 0.35 | 382 |
| N22563 | 0.02 | 0.12 | 0.37 | 0.33 | 0.39 | 383 |
| AI764969 | 0.03 | −0.18 | 0.07 | 0.53 | 0.25 | 384 |
| AA417950 | 0.02 | −0.34 | −0.09 | 0.48 | 0.26 | 385 |
| H15431 | 0.03 | −0.39 | −0.14 | 0.51 | 0.30 | 386 |
| AI147997 | 0.02 | 0.11 | 0.35 | 0.24 | 0.45 | 387 |
| AI378142 | 0.03 | −0.10 | 0.14 | 0.25 | 0.42 | 388 |
| AA528101 | 0.00 | −0.43 | −0.19 | 0.32 | 0.21 | 389 |
| T83761 | 0.04 | −0.41 | −0.16 | 0.36 | 0.46 | 390 |

TABLE 2-continued

Significantly elevated gene activities in samples of patients with infectious MOF, if compared with the gene activities of patients with non-infectious MOF.

| GenBank Accession No. | p-value | Mean normalised and transformed expression value | | Standard deviation | | SEQUENCE-ID |
|---|---|---|---|---|---|---|
| | | Group of patients with non-infectious MOF | Group of patients with infectious MOF | Group of patients with non-infectious MOF | Group of patients with infectious MOF | |
| XM_046674 | 0.04 | −0.80 | −0.56 | 0.59 | 0.21 | 391 |
| AI925556 | 0.00 | −0.53 | −0.29 | 0.24 | 0.21 | 392 |
| N50785 | 0.03 | 0.25 | 0.49 | 0.29 | 0.43 | 393 |
| AI739085 | 0.04 | −0.41 | −0.17 | 0.41 | 0.39 | 394 |
| AA885052 | 0.02 | −0.13 | 0.11 | 0.42 | 0.28 | 395 |
| R45218 | 0.01 | 0.17 | 0.41 | 0.25 | 0.37 | 396 |
| N71365 | 0.00 | −0.39 | −0.15 | 0.22 | 0.33 | 397 |
| AI590053 | 0.00 | −0.38 | −0.14 | 0.19 | 0.16 | 398 |
| NM_013229 | 0.00 | 0.02 | 0.26 | 0.22 | 0.26 | 399 |
| NM_001196 | 0.02 | −0.53 | −0.30 | 0.27 | 0.39 | 400 |
| R94509 | 0.01 | 0.07 | 0.31 | 0.29 | 0.29 | 401 |
| AA282936 | 0.02 | 0.16 | 0.39 | 0.41 | 0.33 | 402 |
| NM_003824 | 0.01 | −0.74 | −0.50 | 0.26 | 0.37 | 403 |
| T65296 | 0.01 | 0.00 | 0.23 | 0.23 | 0.34 | 404 |
| AI583064 | 0.03 | 0.01 | 0.24 | 0.28 | 0.42 | 405 |
| R94626 | 0.01 | −0.25 | −0.01 | 0.25 | 0.35 | 406 |
| AI216612 | 0.03 | −0.20 | 0.03 | 0.42 | 0.35 | 407 |
| NM_015318.1 | 0.01 | −0.12 | 0.11 | 0.32 | 0.25 | 408 |
| AA426397 | 0.02 | −0.37 | −0.14 | 0.33 | 0.34 | 409 |
| H78362 | 0.01 | −0.53 | −0.30 | 0.31 | 0.27 | 410 |
| AA878269 | 0.02 | −0.28 | −0.05 | 0.32 | 0.34 | 411 |
| NM_017778 | 0.01 | −0.17 | 0.06 | 0.39 | 0.26 | 412 |
| AI709236 | 0.00 | −0.24 | −0.01 | 0.21 | 0.28 | 413 |
| AA465175 | 0.01 | −0.11 | 0.12 | 0.32 | 0.27 | 414 |
| AI798573 | 0.00 | −0.34 | −0.12 | 0.18 | 0.21 | 415 |
| NM_139070 | 0.02 | −0.87 | −0.64 | 0.41 | 0.27 | 416 |
| XM_049749 | 0.04 | −0.18 | 0.05 | 0.50 | 0.28 | 417 |
| AI864931 | 0.01 | 0.09 | 0.31 | 0.24 | 0.31 | 418 |
| NM_021975 | 0.00 | −0.63 | −0.41 | 0.29 | 0.22 | 419 |
| R60931 | 0.03 | 0.16 | 0.39 | 0.35 | 0.35 | 420 |
| XM_037260 | 0.00 | −0.38 | −0.15 | 0.18 | 0.26 | 421 |
| R36650 | 0.00 | −0.40 | −0.17 | 0.23 | 0.25 | 422 |
| AA621075 | 0.00 | −0.31 | −0.09 | 0.24 | 0.28 | 423 |
| AI018273 | 0.04 | −0.23 | 0.00 | 0.45 | 0.31 | 424 |
| AI701905 | 0.00 | −0.24 | −0.01 | 0.22 | 0.24 | 425 |
| XM_054686 | 0.02 | −0.55 | −0.33 | 0.30 | 0.31 | 426 |
| NM_139276 | 0.02 | −0.09 | 0.14 | 0.25 | 0.38 | 427 |
| AI418064 | 0.01 | −0.23 | −0.01 | 0.32 | 0.24 | 428 |
| NM_002503 | 0.03 | −0.50 | −0.28 | 0.40 | 0.32 | 429 |
| AI923559 | 0.02 | −0.37 | −0.15 | 0.35 | 0.33 | 430 |
| NM_004295 | 0.04 | −0.66 | −0.44 | 0.40 | 0.37 | 431 |
| AA425105 | 0.03 | −0.19 | 0.04 | 0.43 | 0.29 | 432 |
| NM_002997 | 0.02 | 0.01 | 0.24 | 0.37 | 0.28 | 433 |
| NM_024013 | 0.00 | 0.04 | 0.27 | 0.28 | 0.23 | 434 |
| AA856755 | 0.02 | −0.40 | −0.18 | 0.34 | 0.34 | 435 |
| AI371339 | 0.00 | −0.28 | −0.06 | 0.24 | 0.22 | 436 |
| AA453528 | 0.04 | −0.30 | −0.08 | 0.50 | 0.27 | 437 |
| AI214646 | 0.04 | −0.27 | −0.05 | 0.24 | 0.43 | 438 |
| NM_006724 | 0.01 | −0.45 | −0.22 | 0.32 | 0.24 | 439 |
| AI925740 | 0.02 | 0.02 | 0.24 | 0.42 | 0.25 | 440 |
| H81378 | 0.00 | −0.16 | 0.06 | 0.32 | 0.19 | 441 |
| H82860 | 0.03 | 0.01 | 0.23 | 0.25 | 0.41 | 442 |
| BC032713 | 0.02 | 0.39 | 0.61 | 0.22 | 0.37 | 443 |
| H10036 | 0.05 | −0.08 | 0.13 | 0.42 | 0.35 | 444 |
| AI707917 | 0.00 | −0.34 | −0.12 | 0.18 | 0.20 | 445 |
| AA676928 | 0.05 | −0.04 | 0.18 | 0.36 | 0.40 | 446 |
| AI057616 | 0.00 | −0.03 | 0.19 | 0.19 | 0.30 | 447 |
| NM_003080 | 0.01 | −0.03 | 0.18 | 0.29 | 0.25 | 448 |
| AI685198 | 0.00 | −0.41 | −0.20 | 0.19 | 0.23 | 449 |
| AA436683 | 0.02 | −0.16 | 0.05 | 0.34 | 0.29 | 450 |
| R39456 | 0.00 | −0.34 | −0.13 | 0.17 | 0.23 | 451 |
| NM_004050 | 0.03 | −0.23 | −0.02 | 0.38 | 0.31 | 452 |
| N49208 | 0.02 | 0.13 | 0.34 | 0.35 | 0.32 | 453 |
| XM_055699 | 0.05 | 0.02 | 0.23 | 0.36 | 0.39 | 454 |
| BC028234 | 0.02 | −0.45 | −0.24 | 0.26 | 0.37 | 455 |
| N89900 | 0.02 | −0.39 | −0.18 | 0.36 | 0.28 | 456 |
| NM_001278 | 0.00 | −0.63 | −0.42 | 0.22 | 0.21 | 457 |
| AI921613 | 0.01 | −0.06 | 0.16 | 0.25 | 0.26 | 458 |

TABLE 2-continued

Significantly elevated gene activities in samples of patients with infectious MOF, if compared with the gene activities of patients with non-infectious MOF.

| GenBank Accession No. | p-value | Mean normalised and transformed expression value | | Standard deviation | | SEQUENCE-ID |
|---|---|---|---|---|---|---|
| | | Group of patients with non-infectious MOF | Group of patients with infectious MOF | Group of patients with non-infectious MOF | Group of patients with infectious MOF | |
| NM_003821 | 0.03 | −0.64 | −0.43 | 0.43 | 0.23 | 459 |
| XM_046035 | 0.00 | −0.37 | −0.16 | 0.20 | 0.27 | 460 |
| AI936300 | 0.04 | 0.08 | 0.29 | 0.30 | 0.39 | 461 |
| NM_003131 | 0.00 | −0.71 | −0.50 | 0.30 | 0.21 | 462 |
| R61546 | 0.01 | −0.52 | −0.31 | 0.30 | 0.25 | 463 |
| AA431750 | 0.02 | −0.24 | −0.03 | 0.32 | 0.29 | 464 |
| AI524099 | 0.00 | −0.03 | 0.18 | 0.15 | 0.20 | 465 |
| XM_042665 | 0.00 | 0.07 | 0.28 | 0.25 | 0.22 | 466 |
| AI820873 | 0.02 | −0.48 | −0.27 | 0.39 | 0.24 | 467 |
| NM_019011 | 0.02 | −0.60 | −0.39 | 0.27 | 0.35 | 468 |
| H51585 | 0.05 | −0.57 | −0.36 | 0.42 | 0.30 | 469 |
| AI393173 | 0.02 | −0.04 | 0.16 | 0.25 | 0.34 | 470 |
| AI560205 | 0.00 | −0.36 | −0.15 | 0.19 | 0.23 | 471 |
| AA429020 | 0.00 | −0.31 | −0.11 | 0.20 | 0.17 | 472 |
| NM_000681.2 | 0.01 | 0.14 | 0.34 | 0.30 | 0.27 | 473 |
| NM_014550 | 0.00 | −0.10 | 0.10 | 0.25 | 0.16 | 474 |
| AA453256 | 0.00 | −0.04 | 0.16 | 0.20 | 0.26 | 475 |
| NM_021138 | 0.00 | −0.23 | −0.03 | 0.28 | 0.14 | 476 |
| R51304 | 0.05 | −0.02 | 0.19 | 0.32 | 0.38 | 477 |
| AI590111 | 0.00 | −0.31 | −0.10 | 0.14 | 0.20 | 478 |
| H09305 | 0.01 | −0.57 | −0.37 | 0.31 | 0.26 | 479 |
| R99076 | 0.00 | −0.40 | −0.19 | 0.19 | 0.22 | 480 |
| AI559096 | 0.01 | 0.28 | 0.48 | 0.29 | 0.29 | 481 |
| AI610213 | 0.02 | −0.12 | 0.08 | 0.34 | 0.27 | 482 |
| N66038 | 0.00 | −0.33 | −0.12 | 0.17 | 0.20 | 483 |
| NM_002649 | 0.00 | −0.33 | −0.13 | 0.17 | 0.29 | 484 |
| NM_006676 | 0.02 | −0.54 | −0.34 | 0.32 | 0.27 | 485 |
| NM_014959 | 0.00 | −0.38 | −0.18 | 0.24 | 0.25 | 486 |
| BC013992 | 0.01 | 0.01 | 0.21 | 0.16 | 0.32 | 487 |
| N32057 | 0.02 | −0.34 | −0.14 | 0.39 | 0.20 | 488 |
| AI801695 | 0.00 | −0.33 | −0.13 | 0.17 | 0.18 | 489 |
| AI568793 | 0.03 | 0.11 | 0.31 | 0.29 | 0.33 | 490 |
| AA479285 | 0.00 | 0.08 | 0.27 | 0.23 | 0.23 | 491 |
| H06501 | 0.02 | −0.10 | 0.10 | 0.32 | 0.28 | 492 |
| R00259 | 0.03 | −0.06 | 0.14 | 0.31 | 0.32 | 493 |
| AI362368 | 0.00 | −0.33 | −0.13 | 0.17 | 0.19 | 494 |
| AI635040 | 0.00 | −0.14 | 0.06 | 0.18 | 0.26 | 495 |
| AI354869 | 0.03 | −0.48 | −0.29 | 0.32 | 0.26 | 496 |
| N71407 | 0.02 | 0.06 | 0.25 | 0.26 | 0.32 | 497 |
| XM_038544 | 0.04 | −0.12 | 0.07 | 0.38 | 0.29 | 498 |
| NM_031910 | 0.04 | 0.18 | 0.38 | 0.27 | 0.38 | 499 |
| AI862063 | 0.00 | −0.28 | −0.08 | 0.20 | 0.24 | 500 |
| AA455638 | 0.03 | 0.07 | 0.27 | 0.28 | 0.32 | 501 |
| AI697430 | 0.00 | −0.36 | −0.17 | 0.18 | 0.21 | 502 |
| R42480 | 0.01 | −0.49 | −0.29 | 0.25 | 0.23 | 503 |
| AI674115 | 0.01 | 0.02 | 0.21 | 0.24 | 0.29 | 504 |
| AA968926 | 0.03 | −0.32 | −0.13 | 0.37 | 0.26 | 505 |
| AI524694 | 0.00 | −0.38 | −0.19 | 0.18 | 0.23 | 506 |
| AA609857 | 0.02 | −0.08 | 0.12 | 0.30 | 0.29 | 507 |
| AI913713 | 0.01 | −0.46 | −0.27 | 0.33 | 0.21 | 508 |
| W04695 | 0.00 | −0.28 | −0.09 | 0.16 | 0.24 | 509 |
| NM_033012 | 0.04 | −0.12 | 0.07 | 0.35 | 0.31 | 510 |
| T77048 | 0.02 | −0.01 | 0.18 | 0.26 | 0.31 | 511 |
| AI817381 | 0.01 | −0.25 | −0.06 | 0.23 | 0.24 | 512 |
| AI624918 | 0.03 | −0.02 | 0.17 | 0.28 | 0.32 | 513 |
| AI888072 | 0.01 | −0.26 | −0.07 | 0.23 | 0.26 | 514 |
| AA883759 | 0.00 | −0.38 | −0.20 | 0.21 | 0.22 | 515 |
| AA478611 | 0.00 | −0.34 | −0.15 | 0.25 | 0.17 | 516 |
| AI452862 | 0.03 | −0.28 | −0.09 | 0.34 | 0.26 | 517 |
| AI277955 | 0.00 | −0.46 | −0.27 | 0.24 | 0.22 | 518 |
| AI520967 | 0.00 | −0.34 | −0.15 | 0.17 | 0.20 | 519 |
| T91937 | 0.05 | 0.36 | 0.54 | 0.27 | 0.37 | 520 |
| AA993698 | 0.00 | 0.01 | 0.20 | 0.21 | 0.20 | 521 |
| AI620374 | 0.00 | −0.40 | −0.22 | 0.18 | 0.22 | 522 |
| AA707628 | 0.00 | −0.27 | −0.08 | 0.12 | 0.17 | 523 |
| AI572545 | 0.01 | −0.38 | −0.19 | 0.17 | 0.28 | 524 |
| AI801540 | 0.04 | −0.16 | 0.03 | 0.36 | 0.28 | 525 |
| AI354889 | 0.00 | −0.11 | 0.07 | 0.22 | 0.18 | 526 |

TABLE 2-continued

Significantly elevated gene activities in samples of patients with infectious MOF, if compared with the gene activities of patients with non-infectious MOF.

| GenBank Accession No. | p-value | Mean normalised and transformed expression value | | Standard deviation | | SEQUENCE-ID |
|---|---|---|---|---|---|---|
| | | Group of patients with non-infectious MOF | Group of patients with infectious MOF | Group of patients with non-infectious MOF | Group of patients with infectious MOF | |
| NM_030751 | 0.03 | −0.09 | 0.09 | 0.33 | 0.25 | 527 |
| NM_000657 | 0.01 | −0.50 | −0.32 | 0.27 | 0.22 | 528 |
| AA045139 | 0.02 | −0.43 | −0.24 | 0.34 | 0.23 | 529 |
| AI912148 | 0.00 | −0.25 | −0.06 | 0.18 | 0.20 | 530 |
| AA513806 | 0.04 | −0.21 | −0.03 | 0.29 | 0.32 | 531 |
| H48440 | 0.00 | −0.35 | −0.17 | 0.16 | 0.23 | 532 |
| AA114117 | 0.00 | −0.38 | −0.20 | 0.17 | 0.18 | 533 |
| AI654471 | 0.00 | −0.20 | −0.02 | 0.19 | 0.20 | 534 |
| AA423792 | 0.00 | −0.16 | 0.02 | 0.14 | 0.25 | 535 |
| AI926484 | 0.00 | −0.08 | 0.10 | 0.25 | 0.14 | 536 |
| T89979 | 0.00 | −0.30 | −0.12 | 0.16 | 0.19 | 537 |
| AI889310 | 0.01 | −0.25 | −0.07 | 0.26 | 0.21 | 538 |
| R11261 | 0.04 | −0.27 | −0.09 | 0.43 | 0.18 | 539 |
| AI932551 | 0.00 | −0.32 | −0.14 | 0.16 | 0.23 | 540 |
| NM_017626.1 | 0.01 | −0.56 | −0.38 | 0.22 | 0.26 | 541 |
| AI381513 | 0.04 | −0.29 | −0.11 | 0.32 | 0.29 | 542 |
| AA682407 | 0.02 | −0.24 | −0.07 | 0.25 | 0.29 | 543 |
| AA954316 | 0.04 | −0.75 | −0.57 | 0.35 | 0.27 | 544 |
| AI791500 | 0.02 | 0.16 | 0.34 | 0.18 | 0.31 | 545 |
| T91881 | 0.00 | −0.26 | −0.08 | 0.18 | 0.23 | 546 |
| AI149857 | 0.02 | −0.06 | 0.12 | 0.18 | 0.30 | 547 |
| AI370842 | 0.04 | 0.11 | 0.29 | 0.31 | 0.30 | 548 |
| AA401205 | 0.00 | −0.13 | 0.05 | 0.18 | 0.19 | 549 |
| AA453267 | 0.02 | −0.03 | 0.15 | 0.26 | 0.28 | 550 |
| R88475 | 0.00 | −0.35 | −0.17 | 0.18 | 0.20 | 551 |
| AI864919 | 0.01 | −0.38 | −0.20 | 0.19 | 0.25 | 552 |
| NM_002169 | 0.04 | −0.24 | −0.07 | 0.33 | 0.27 | 553 |
| R46801 | 0.05 | 0.27 | 0.44 | 0.35 | 0.27 | 554 |
| AI277856 | 0.02 | −0.12 | 0.06 | 0.22 | 0.27 | 555 |
| H22921 | 0.00 | −0.33 | −0.15 | 0.19 | 0.22 | 556 |
| AI763386 | 0.03 | −0.37 | −0.20 | 0.30 | 0.27 | 557 |
| N78812 | 0.01 | −0.23 | −0.06 | 0.25 | 0.20 | 558 |
| H83981 | 0.04 | 0.04 | 0.22 | 0.28 | 0.30 | 559 |
| AA029887 | 0.00 | −0.40 | −0.22 | 0.19 | 0.21 | 560 |
| AI192112 | 0.00 | −0.11 | 0.06 | 0.15 | 0.24 | 561 |
| W88960 | 0.01 | 0.10 | 0.28 | 0.21 | 0.24 | 562 |
| W80744 | 0.00 | −0.25 | −0.08 | 0.15 | 0.21 | 563 |
| AI521577 | 0.01 | −0.31 | −0.13 | 0.18 | 0.23 | 564 |
| AA418572 | 0.01 | −0.13 | 0.05 | 0.17 | 0.25 | 565 |
| N73510 | 0.00 | −0.38 | −0.21 | 0.17 | 0.22 | 566 |
| AI631299 | 0.03 | −0.16 | 0.01 | 0.24 | 0.29 | 567 |
| XM_012717 | 0.00 | −0.44 | −0.27 | 0.18 | 0.17 | 568 |
| NM_000590 | 0.03 | 0.32 | 0.50 | 0.23 | 0.29 | 569 |
| AI381910 | 0.01 | −0.04 | 0.13 | 0.21 | 0.23 | 570 |
| R87714 | 0.04 | −0.18 | −0.01 | 0.33 | 0.23 | 571 |
| AA609628 | 0.00 | −0.36 | −0.19 | 0.17 | 0.19 | 572 |
| AA634317 | 0.03 | 0.19 | 0.36 | 0.27 | 0.28 | 573 |
| AI214830 | 0.04 | −0.27 | −0.10 | 0.23 | 0.32 | 574 |
| AI203201 | 0.04 | −0.26 | −0.09 | 0.26 | 0.29 | 575 |
| AI924806 | 0.00 | −0.29 | −0.12 | 0.20 | 0.18 | 576 |
| AA701319 | 0.02 | −0.07 | 0.10 | 0.22 | 0.28 | 577 |
| N63628 | 0.03 | −0.26 | −0.09 | 0.26 | 0.27 | 578 |
| R02742 | 0.04 | −0.17 | −0.01 | 0.32 | 0.25 | 579 |
| H07860 | 0.02 | −0.03 | 0.13 | 0.26 | 0.24 | 580 |
| H77534 | 0.02 | −0.35 | −0.18 | 0.32 | 0.20 | 581 |
| AI208537 | 0.02 | −0.21 | −0.04 | 0.34 | 0.17 | 582 |
| AI184715 | 0.01 | −0.03 | 0.13 | 0.23 | 0.20 | 583 |
| R05816 | 0.00 | −0.27 | −0.10 | 0.19 | 0.20 | 584 |
| AA961252 | 0.04 | −0.14 | 0.02 | 0.26 | 0.31 | 585 |
| AI801425 | 0.00 | −0.21 | −0.04 | 0.22 | 0.17 | 586 |
| AA477776 | 0.01 | −0.01 | 0.16 | 0.21 | 0.20 | 587 |
| R06585 | 0.01 | −0.40 | −0.23 | 0.18 | 0.21 | 588 |
| AA405788 | 0.01 | −0.36 | −0.19 | 0.15 | 0.25 | 589 |
| R06107 | 0.01 | −0.23 | −0.07 | 0.24 | 0.19 | 590 |
| AA923316 | 0.00 | −0.20 | −0.04 | 0.15 | 0.19 | 591 |
| AI421397 | 0.02 | −0.02 | 0.14 | 0.19 | 0.26 | 592 |
| NM_006881 | 0.01 | −0.40 | −0.24 | 0.20 | 0.23 | 593 |
| R43415 | 0.00 | −0.24 | −0.08 | 0.14 | 0.19 | 594 |

TABLE 2-continued

Significantly elevated gene activities in samples of patients with infectious MOF, if compared with the gene activities of patients with non-infectious MOF.

| GenBank Accession No. | p-value | Mean normalised and transformed expression value | | Standard deviation | | SEQUENCE-ID |
|---|---|---|---|---|---|---|
| | | Group of patients with non-infectious MOF | Group of patients with infectious MOF | Group of patients with non-infectious MOF | Group of patients with infectious MOF | |
| H11495 | 0.01 | −0.29 | −0.12 | 0.26 | 0.13 | 595 |
| AI208772 | 0.04 | −0.23 | −0.07 | 0.29 | 0.27 | 596 |
| AA479784 | 0.03 | −0.06 | 0.10 | 0.29 | 0.24 | 597 |
| AA485092 | 0.00 | −0.36 | −0.20 | 0.16 | 0.20 | 598 |
| AA664688 | 0.00 | −0.39 | −0.23 | 0.18 | 0.20 | 599 |
| H48230 | 0.01 | −0.29 | −0.13 | 0.19 | 0.21 | 600 |
| AI248075 | 0.02 | −0.12 | 0.04 | 0.25 | 0.22 | 601 |
| AA418695 | 0.04 | −0.01 | 0.15 | 0.21 | 0.31 | 602 |
| AI673731 | 0.01 | −0.41 | −0.25 | 0.16 | 0.22 | 603 |
| XM_008948 | 0.03 | 0.10 | 0.26 | 0.26 | 0.26 | 604 |
| AI301257 | 0.00 | −0.31 | −0.15 | 0.19 | 0.19 | 605 |
| NM_003823 | 0.04 | −0.72 | −0.56 | 0.31 | 0.24 | 606 |
| AI744264 | 0.01 | −0.14 | 0.02 | 0.16 | 0.22 | 607 |
| AI809873 | 0.03 | −0.45 | −0.29 | 0.24 | 0.26 | 608 |
| AI354243 | 0.01 | −0.34 | −0.18 | 0.17 | 0.21 | 609 |
| NM_001553.1 | 0.04 | −0.15 | 0.01 | 0.27 | 0.27 | 610 |
| W86575 | 0.02 | −0.34 | −0.18 | 0.23 | 0.24 | 611 |
| AA442720 | 0.03 | −0.15 | 0.01 | 0.27 | 0.24 | 612 |
| AA993597 | 0.03 | 0.17 | 0.33 | 0.26 | 0.24 | 613 |
| AI433952 | 0.01 | −0.30 | −0.14 | 0.16 | 0.23 | 614 |
| R56800 | 0.01 | −0.09 | 0.06 | 0.17 | 0.21 | 615 |
| AA417031 | 0.01 | −0.21 | −0.06 | 0.19 | 0.23 | 616 |
| R53961 | 0.04 | −0.45 | −0.29 | 0.28 | 0.25 | 617 |
| T86887 | 0.00 | −0.23 | −0.08 | 0.13 | 0.20 | 618 |
| AA705808 | 0.01 | −0.20 | −0.04 | 0.25 | 0.18 | 619 |
| AA426451 | 0.00 | −0.28 | −0.13 | 0.16 | 0.19 | 620 |
| H06263 | 0.00 | −0.28 | −0.12 | 0.14 | 0.17 | 621 |
| AA659421 | 0.00 | −0.32 | −0.17 | 0.14 | 0.16 | 622 |
| AI801595 | 0.00 | −0.28 | −0.13 | 0.16 | 0.19 | 623 |
| AI672318 | 0.04 | −0.20 | −0.05 | 0.31 | 0.24 | 624 |
| AI762019 | 0.01 | −0.25 | −0.09 | 0.19 | 0.21 | 625 |
| N92873 | 0.02 | −0.11 | 0.05 | 0.28 | 0.19 | 626 |
| NM_017442 | 0.04 | 0.08 | 0.23 | 0.28 | 0.25 | 627 |
| H46164 | 0.03 | 0.03 | 0.18 | 0.21 | 0.27 | 628 |
| T83946 | 0.01 | −0.29 | −0.14 | 0.20 | 0.21 | 629 |
| AA868726 | 0.04 | −0.42 | −0.27 | 0.26 | 0.25 | 630 |
| H88129 | 0.02 | −0.37 | −0.22 | 0.21 | 0.23 | 631 |
| R88267 | 0.04 | −0.12 | 0.03 | 0.30 | 0.23 | 632 |
| AI798545 | 0.01 | −0.32 | −0.17 | 0.17 | 0.19 | 633 |
| N57775 | 0.02 | −0.14 | 0.01 | 0.22 | 0.22 | 634 |
| AA425134 | 0.00 | −0.21 | −0.07 | 0.16 | 0.19 | 635 |
| AI744807 | 0.01 | −0.59 | −0.44 | 0.20 | 0.22 | 636 |
| AI702056 | 0.05 | −0.27 | −0.12 | 0.22 | 0.29 | 637 |
| NM_000575 | 0.04 | −0.27 | −0.12 | 0.23 | 0.25 | 638 |
| T98779 | 0.01 | −0.38 | −0.23 | 0.18 | 0.23 | 639 |
| NM_000587 | 0.01 | −0.43 | −0.28 | 0.18 | 0.19 | 640 |
| R92455 | 0.01 | −0.36 | −0.21 | 0.17 | 0.21 | 641 |
| AI758473 | 0.01 | −0.36 | −0.21 | 0.18 | 0.22 | 642 |
| AA398364 | 0.00 | −0.31 | −0.17 | 0.13 | 0.21 | 643 |
| AI811774 | 0.05 | 0.20 | 0.35 | 0.23 | 0.27 | 644 |
| AI299411 | 0.00 | −0.24 | −0.10 | 0.17 | 0.18 | 645 |
| AA225138 | 0.00 | −0.26 | −0.11 | 0.12 | 0.17 | 646 |
| AA418689 | 0.05 | 0.09 | 0.24 | 0.21 | 0.28 | 647 |
| T77995 | 0.01 | −0.18 | −0.04 | 0.21 | 0.20 | 648 |
| AA808788 | 0.04 | −0.33 | −0.18 | 0.18 | 0.25 | 649 |
| AI677645 | 0.01 | −0.25 | −0.11 | 0.15 | 0.19 | 650 |
| AA629306 | 0.04 | −0.07 | 0.07 | 0.26 | 0.24 | 651 |
| AA749151 | 0.00 | −0.19 | −0.05 | 0.13 | 0.17 | 652 |
| AI679294 | 0.01 | −0.41 | −0.27 | 0.19 | 0.19 | 653 |
| R45611 | 0.02 | −0.24 | −0.10 | 0.16 | 0.24 | 654 |
| NM_000588 | 0.05 | −0.18 | −0.04 | 0.29 | 0.22 | 655 |
| H99483 | 0.01 | −0.29 | −0.15 | 0.16 | 0.22 | 656 |
| AI679923 | 0.01 | −0.46 | −0.32 | 0.17 | 0.20 | 657 |
| AI077580 | 0.05 | −0.04 | 0.10 | 0.27 | 0.23 | 658 |
| D49410 | 0.01 | −0.31 | −0.17 | 0.19 | 0.19 | 659 |
| AI692267 | 0.04 | −0.42 | −0.28 | 0.22 | 0.24 | 660 |
| AI804001 | 0.02 | 0.00 | 0.14 | 0.19 | 0.23 | 661 |
| T87188 | 0.01 | −0.32 | −0.18 | 0.19 | 0.19 | 662 |

TABLE 2-continued

Significantly elevated gene activities in samples of patients with infectious MOF, if compared with the gene activities of patients with non-infectious MOF.

| GenBank Accession No. | p-value | Mean normalised and transformed expression value | | Standard deviation | | SEQUENCE-ID |
|---|---|---|---|---|---|---|
| | | Group of patients with non-infectious MOF | Group of patients with infectious MOF | Group of patients with non-infectious MOF | Group of patients with infectious MOF | |
| AI368218 | 0.02 | −0.24 | −0.10 | 0.13 | 0.23 | 663 |
| AI208749 | 0.02 | −0.02 | 0.11 | 0.22 | 0.19 | 664 |
| H61046 | 0.02 | −0.21 | −0.07 | 0.18 | 0.22 | 665 |
| NM_001330.1 | 0.01 | −0.05 | 0.08 | 0.19 | 0.20 | 666 |
| XM_001322 | 0.01 | −0.33 | −0.19 | 0.18 | 0.17 | 667 |
| NM_004195 | 0.04 | 0.23 | 0.37 | 0.16 | 0.27 | 668 |
| AI285713 | 0.01 | −0.32 | −0.18 | 0.15 | 0.21 | 669 |
| AA527369 | 0.00 | −0.13 | 0.00 | 0.15 | 0.16 | 670 |
| AI350069 | 0.01 | −0.24 | −0.11 | 0.15 | 0.21 | 671 |
| AI493975 | 0.01 | −0.24 | −0.10 | 0.18 | 0.16 | 672 |
| AI355007 | 0.03 | −0.23 | −0.10 | 0.22 | 0.21 | 673 |
| AA225239 | 0.04 | −0.40 | −0.26 | 0.21 | 0.25 | 674 |
| AA001392 | 0.03 | −0.39 | −0.26 | 0.24 | 0.19 | 675 |
| AI933797 | 0.02 | −0.28 | −0.15 | 0.22 | 0.18 | 676 |
| R43065 | 0.01 | −0.21 | −0.08 | 0.16 | 0.18 | 677 |
| AA478621 | 0.03 | −0.21 | −0.08 | 0.21 | 0.20 | 678 |
| AA012850 | 0.03 | −0.32 | −0.19 | 0.17 | 0.22 | 679 |
| AI925035 | 0.03 | −0.15 | −0.02 | 0.17 | 0.23 | 680 |
| AA995218 | 0.03 | −0.22 | −0.09 | 0.19 | 0.21 | 681 |
| AA897716 | 0.04 | −0.18 | −0.06 | 0.23 | 0.21 | 682 |
| AA983987 | 0.02 | −0.28 | −0.15 | 0.18 | 0.18 | 683 |
| AI762202 | 0.03 | −0.18 | −0.05 | 0.22 | 0.20 | 684 |
| T95909 | 0.02 | −0.34 | −0.22 | 0.18 | 0.19 | 685 |
| N22551 | 0.03 | −0.36 | −0.24 | 0.17 | 0.22 | 686 |
| AI769053 | 0.03 | −0.28 | −0.15 | 0.15 | 0.22 | 687 |
| AF039955 | 0.01 | −0.37 | −0.24 | 0.20 | 0.16 | 688 |
| AI935874 | 0.02 | −0.26 | −0.14 | 0.16 | 0.20 | 689 |
| AI570779 | 0.01 | −0.31 | −0.19 | 0.15 | 0.18 | 690 |
| AI240539 | 0.01 | −0.22 | −0.09 | 0.17 | 0.18 | 691 |
| H54423 | 0.03 | −0.32 | −0.20 | 0.16 | 0.22 | 692 |
| AA460136 | 0.02 | −0.09 | 0.03 | 0.24 | 0.14 | 693 |
| NM_033357 | 0.05 | −0.24 | −0.12 | 0.19 | 0.23 | 694 |
| AI923479 | 0.04 | −0.30 | −0.18 | 0.20 | 0.22 | 695 |
| H18944 | 0.04 | −0.42 | −0.30 | 0.21 | 0.19 | 696 |
| NM_006509 | 0.03 | 0.01 | 0.13 | 0.12 | 0.23 | 697 |
| AI865298 | 0.02 | −0.31 | −0.19 | 0.13 | 0.20 | 698 |
| AI123502 | 0.04 | −0.36 | −0.24 | 0.17 | 0.22 | 699 |
| AI885918 | 0.02 | −0.24 | −0.12 | 0.14 | 0.19 | 700 |
| AA225023 | 0.02 | −0.33 | −0.21 | 0.12 | 0.20 | 701 |
| AA421020 | 0.04 | −0.25 | −0.13 | 0.19 | 0.21 | 702 |
| AJ297560 | 0.05 | −0.29 | −0.17 | 0.21 | 0.20 | 703 |
| N95217 | 0.02 | −0.30 | −0.19 | 0.12 | 0.19 | 704 |
| AA526032 | 0.04 | −0.25 | −0.13 | 0.20 | 0.19 | 705 |
| AA496309 | 0.02 | −0.32 | −0.20 | 0.15 | 0.19 | 706 |
| AI732958 | 0.03 | −0.22 | −0.11 | 0.18 | 0.18 | 707 |
| AA410828 | 0.02 | −0.29 | −0.18 | 0.20 | 0.16 | 708 |
| AA453993 | 0.02 | −0.30 | −0.19 | 0.18 | 0.16 | 709 |
| R92993 | 0.02 | −0.26 | −0.15 | 0.12 | 0.19 | 710 |
| NM_003921 | 0.04 | −0.23 | −0.13 | 0.20 | 0.18 | 711 |
| AI379967 | 0.02 | −0.34 | −0.23 | 0.15 | 0.17 | 712 |
| AI926656 | 0.04 | −0.26 | −0.15 | 0.18 | 0.19 | 713 |
| AA935872 | 0.03 | −0.31 | −0.20 | 0.16 | 0.18 | 714 |
| H08791 | 0.03 | −0.27 | −0.17 | 0.16 | 0.18 | 715 |
| AI932884 | 0.03 | −0.31 | −0.21 | 0.16 | 0.18 | 716 |
| AI926745 | 0.03 | −0.33 | −0.22 | 0.18 | 0.16 | 717 |
| R99595 | 0.05 | −0.29 | −0.19 | 0.16 | 0.20 | 718 |
| AI824579 | 0.03 | −0.31 | −0.21 | 0.13 | 0.18 | 719 |
| AA427886 | 0.03 | −0.27 | −0.17 | 0.14 | 0.16 | 720 |
| H42488 | 0.04 | −0.33 | −0.24 | 0.16 | 0.15 | 721 |

TABLE 3

Significantly under-expressed gene activities in samples of patients with infectious MODS/MOF, if compared with the gene activities of patients with non-infectious MODS/MOF.

| GenBank Accession No. | p-value | Mean normalised and transformed expression value | | Standard deviation | | SEQUENCE-ID |
|---|---|---|---|---|---|---|
| | | Group of patients with non-infectious MOF | Group of patients with infectious MOF | Group of patients with non-infectious MOF | Group of patients with infectious MOF | |
| NM_019111 | 0.00 | 1.41 | 0.21 | 0.73 | 0.56 | 722 |
| N29761 | 0.00 | −0.25 | −1.35 | 0.61 | 0.92 | 723 |
| NM_002124 | 0.00 | 1.60 | 0.54 | 0.62 | 0.52 | 724 |
| R43910 | 0.00 | 2.51 | 1.49 | 1.25 | 0.88 | 725 |
| NM_000570 | 0.00 | 3.66 | 2.67 | 0.70 | 1.31 | 726 |
| NM_002923 | 0.00 | 2.03 | 1.07 | 0.83 | 0.89 | 727 |
| X00457 | 0.00 | 1.46 | 0.50 | 0.84 | 0.60 | 728 |
| NM_022555 | 0.00 | 1.86 | 0.91 | 0.58 | 0.54 | 729 |
| NM_002125 | 0.00 | 1.38 | 0.46 | 0.55 | 0.45 | 730 |
| AA620760 | 0.00 | 0.30 | −0.62 | 0.47 | 0.60 | 731 |
| NM_000569 | 0.01 | 3.13 | 2.26 | 0.86 | 1.21 | 732 |
| NM_021983 | 0.00 | 1.38 | 0.52 | 0.48 | 0.41 | 733 |
| R43203 | 0.00 | 2.03 | 1.18 | 1.16 | 0.74 | 734 |
| NM_033554 | 0.00 | 1.42 | 0.60 | 0.60 | 0.52 | 735 |
| AA626239 | 0.00 | 0.15 | −0.65 | 0.74 | 0.73 | 736 |
| NM_007328 | 0.00 | −0.31 | −1.10 | 0.49 | 0.64 | 737 |
| M90746 | 0.02 | 3.67 | 2.89 | 0.74 | 1.37 | 738 |
| T91086 | 0.00 | −0.81 | −1.59 | 0.63 | 0.67 | 739 |
| AA151104 | 0.00 | 0.11 | −0.64 | 0.46 | 0.46 | 740 |
| H45298 | 0.01 | 1.84 | 1.09 | 0.90 | 0.97 | 741 |
| NM_031311 | 0.00 | 0.78 | 0.03 | 0.52 | 0.39 | 742 |
| AI590144 | 0.00 | 1.70 | 0.96 | 0.97 | 0.70 | 743 |
| NM_001824.2 | 0.00 | 1.63 | 0.88 | 0.58 | 0.67 | 744 |
| NM_018643 | 0.00 | 1.70 | 0.96 | 0.54 | 0.66 | 745 |
| AA400790 | 0.00 | 0.93 | 0.20 | 0.59 | 0.52 | 746 |
| NM_001251 | 0.00 | 1.18 | 0.47 | 0.42 | 0.48 | 747 |
| NM_000887.2 | 0.00 | 0.24 | −0.48 | 0.92 | 0.61 | 748 |
| AI696291 | 0.00 | 0.74 | 0.04 | 0.64 | 0.39 | 749 |
| NM_031477 | 0.02 | 1.89 | 1.19 | 1.02 | 1.06 | 750 |
| AA910846 | 0.00 | 1.29 | 0.60 | 0.87 | 0.45 | 751 |
| NM_005538 | 0.00 | 1.59 | 0.91 | 0.90 | 0.72 | 752 |
| AA398331 | 0.00 | 0.13 | −0.53 | 0.51 | 0.46 | 753 |
| NM_025139 | 0.04 | −1.79 | −2.41 | 0.75 | 1.17 | 754 |
| AA398611 | 0.00 | 1.16 | 0.54 | 0.77 | 0.43 | 755 |
| NM_006682 | 0.00 | −0.05 | −0.67 | 0.46 | 0.39 | 756 |
| X52473 | 0.00 | 1.71 | 1.09 | 0.59 | 0.74 | 757 |
| AI859777 | 0.01 | −1.02 | −1.63 | 0.87 | 0.77 | 758 |
| H18649 | 0.00 | −0.41 | −1.01 | 0.30 | 0.58 | 759 |
| AI700444 | 0.00 | 1.57 | 0.97 | 0.70 | 0.63 | 760 |
| XM_001472 | 0.00 | −0.36 | −0.95 | 0.61 | 0.59 | 761 |
| XM_049959 | 0.01 | 2.10 | 1.53 | 0.73 | 0.78 | 762 |
| AA863064 | 0.03 | 0.96 | 0.39 | 1.20 | 0.63 | 763 |
| H88328 | 0.01 | −1.27 | −1.84 | 0.73 | 0.69 | 764 |
| R40861 | 0.00 | 0.82 | 0.25 | 0.82 | 0.51 | 765 |
| AI733498 | 0.00 | −0.37 | −0.93 | 0.36 | 0.58 | 766 |
| NM_002621 | 0.01 | 1.16 | 0.61 | 0.63 | 0.70 | 767 |
| AI732971 | 0.00 | 0.46 | −0.09 | 0.55 | 0.35 | 768 |
| AA813145 | 0.00 | 0.48 | −0.07 | 0.40 | 0.41 | 769 |
| NM_004221.2 | 0.02 | 2.05 | 1.51 | 0.75 | 0.79 | 770 |
| AA740907 | 0.00 | 0.05 | −0.49 | 0.44 | 0.32 | 771 |
| NM_032022 | 0.00 | 0.90 | 0.36 | 0.42 | 0.50 | 772 |
| XM_003789 | 0.00 | −0.25 | −0.78 | 0.37 | 0.47 | 773 |
| AI357099 | 0.02 | −1.06 | −1.59 | 0.85 | 0.78 | 774 |
| NM_003937 | 0.00 | −0.43 | −0.95 | 0.44 | 0.44 | 775 |
| NM_002122 | 0.00 | 0.84 | 0.33 | 0.71 | 0.51 | 776 |
| AI625626 | 0.01 | 0.90 | 0.40 | 0.87 | 0.52 | 777 |
| H23819 | 0.00 | 0.97 | 0.46 | 0.62 | 0.47 | 778 |
| AI797009 | 0.01 | 0.64 | 0.14 | 0.85 | 0.57 | 779 |
| XM_031354 | 0.01 | 0.99 | 0.49 | 0.63 | 0.72 | 780 |
| XM_051958 | 0.01 | 1.20 | 0.70 | 0.53 | 0.72 | 781 |
| AI499173 | 0.01 | 0.11 | −0.38 | 0.75 | 0.50 | 782 |
| NM_000591 | 0.00 | 0.92 | 0.43 | 0.50 | 0.55 | 783 |
| NM_057158 | 0.00 | −0.03 | −0.52 | 0.49 | 0.34 | 784 |
| R71775 | 0.00 | 0.42 | −0.07 | 0.61 | 0.55 | 785 |
| AI924028 | 0.00 | −0.35 | −0.84 | 0.36 | 0.58 | 786 |
| R39504 | 0.00 | −0.50 | −0.98 | 0.34 | 0.40 | 787 |
| N66205 | 0.01 | 1.49 | 1.02 | 0.72 | 0.62 | 788 |
| AI738831 | 0.00 | 0.09 | −0.38 | 0.29 | 0.56 | 789 |

TABLE 3-continued

Significantly under-expressed gene activities in samples of patients with infectious MODS/MOF, if compared with the gene activities of patients with non-infectious MODS/MOF.

| GenBank Accession No. | p-value | Mean normalised and transformed expression value | | Standard deviation | | SEQUENCE-ID |
|---|---|---|---|---|---|---|
| | | Group of patients with non-infectious MOF | Group of patients with infectious MOF | Group of patients with non-infectious MOF | Group of patients with infectious MOF | |
| H18435 | 0.00 | 0.34 | −0.14 | 0.43 | 0.32 | 790 |
| R39782 | 0.00 | −0.35 | −0.82 | 0.44 | 0.35 | 791 |
| R38717 | 0.00 | −0.16 | −0.63 | 0.43 | 0.48 | 792 |
| H96798 | 0.00 | 0.19 | −0.27 | 0.47 | 0.53 | 793 |
| N72174 | 0.02 | 0.92 | 0.46 | 0.53 | 0.73 | 794 |
| AI739381 | 0.00 | −0.11 | −0.57 | 0.24 | 0.50 | 795 |
| AI654546 | 0.00 | 0.05 | −0.41 | 0.31 | 0.46 | 796 |
| AI097494 | 0.00 | −0.72 | −1.19 | 0.41 | 0.57 | 797 |
| NM_000612.2 | 0.00 | 0.93 | 0.47 | 0.50 | 0.36 | 798 |
| AI651536 | 0.00 | 0.62 | 0.16 | 0.50 | 0.29 | 799 |
| AI804425 | 0.00 | 0.90 | 0.44 | 0.73 | 0.38 | 800 |
| n67686 | 0.00 | 0.43 | −0.03 | 0.62 | 0.38 | 801 |
| NM_000062 | 0.01 | −0.18 | −0.63 | 0.75 | 0.45 | 802 |
| R54442 | 0.00 | 0.69 | 0.24 | 0.53 | 0.39 | 803 |
| AI475085 | 0.00 | 0.25 | −0.20 | 0.67 | 0.29 | 804 |
| AI700612 | 0.01 | −0.85 | −1.30 | 0.60 | 0.61 | 805 |
| AA447615 | 0.00 | 0.18 | −0.27 | 0.60 | 0.30 | 806 |
| AI223092 | 0.00 | −0.38 | −0.82 | 0.30 | 0.56 | 807 |
| AI262894 | 0.00 | 0.47 | 0.03 | 0.61 | 0.39 | 808 |
| R52949 | 0.01 | −1.08 | −1.52 | 0.44 | 0.72 | 809 |
| AA629034 | 0.00 | −0.13 | −0.57 | 0.37 | 0.33 | 810 |
| R12559 | 0.00 | 0.72 | 0.29 | 0.45 | 0.37 | 811 |
| AA910310 | 0.00 | 0.03 | −0.40 | 0.35 | 0.27 | 812 |
| NM_006850 | 0.01 | 0.19 | −0.24 | 0.59 | 0.51 | 813 |
| AI689080 | 0.05 | 1.34 | 0.91 | 0.74 | 0.78 | 814 |
| R23755 | 0.00 | 0.16 | −0.26 | 0.40 | 0.37 | 815 |
| N95041 | 0.00 | 0.17 | −0.25 | 0.30 | 0.40 | 816 |
| AA443712 | 0.01 | 0.76 | 0.34 | 0.72 | 0.41 | 817 |
| NM_033302 | 0.03 | 1.53 | 1.11 | 0.54 | 0.72 | 818 |
| AI700810 | 0.00 | 0.59 | 0.18 | 0.72 | 0.25 | 819 |
| XM_004011 | 0.00 | 0.52 | 0.11 | 0.44 | 0.35 | 820 |
| H11433 | 0.00 | 0.38 | −0.03 | 0.55 | 0.35 | 821 |
| NM_006890 | 0.03 | 1.14 | 0.73 | 0.77 | 0.52 | 822 |
| NM_138556 | 0.00 | 0.16 | −0.25 | 0.23 | 0.36 | 823 |
| XM_003937 | 0.00 | 0.13 | −0.28 | 0.34 | 0.33 | 824 |
| NM_000908.1 | 0.00 | −0.05 | −0.46 | 0.22 | 0.30 | 825 |
| NM_017567 | 0.01 | −0.52 | −0.92 | 0.57 | 0.47 | 826 |
| R89802 | 0.00 | −0.21 | −0.61 | 0.27 | 0.33 | 827 |
| NM_000715 | 0.01 | 0.77 | 0.37 | 0.56 | 0.46 | 828 |
| AI924733 | 0.00 | −0.60 | −1.00 | 0.37 | 0.50 | 829 |
| AI859370 | 0.00 | 0.17 | −0.23 | 0.16 | 0.24 | 830 |
| AI023558 | 0.00 | −0.41 | −0.80 | 0.23 | 0.37 | 831 |
| AA021303 | 0.00 | 0.19 | −0.20 | 0.58 | 0.25 | 832 |
| R69609 | 0.01 | 1.03 | 0.64 | 0.54 | 0.51 | 833 |
| XM_057445 | 0.00 | 0.27 | −0.12 | 0.35 | 0.39 | 834 |
| AA046302 | 0.00 | −0.10 | −0.49 | 0.36 | 0.33 | 835 |
| AI383451 | 0.01 | 0.26 | −0.13 | 0.53 | 0.40 | 836 |
| AA464191 | 0.00 | −0.46 | −0.84 | 0.32 | 0.41 | 837 |
| AA425808 | 0.00 | −0.22 | −0.61 | 0.25 | 0.51 | 838 |
| XM_038024 | 0.00 | 0.18 | −0.21 | 0.28 | 0.47 | 839 |
| AI016127 | 0.01 | 1.07 | 0.69 | 0.56 | 0.42 | 840 |
| AA400144 | 0.03 | −0.41 | −0.79 | 0.60 | 0.62 | 841 |
| R43074 | 0.00 | −0.99 | −1.36 | 0.28 | 0.51 | 842 |
| AI628936 | 0.01 | −0.65 | −1.03 | 0.41 | 0.51 | 843 |
| AA461499 | 0.00 | −0.16 | −0.54 | 0.39 | 0.38 | 844 |
| AI668673 | 0.00 | 0.34 | −0.03 | 0.35 | 0.50 | 845 |
| AI539443 | 0.00 | 0.24 | −0.13 | 0.39 | 0.43 | 846 |
| AA404231 | 0.04 | −0.14 | −0.52 | 0.52 | 0.69 | 847 |
| AI692869 | 0.01 | 0.72 | 0.34 | 0.30 | 0.53 | 848 |
| AI822099 | 0.00 | 0.00 | −0.37 | 0.51 | 0.34 | 849 |
| R20616 | 0.00 | 0.12 | −0.25 | 0.30 | 0.32 | 850 |
| AA453406 | 0.01 | −0.66 | −1.03 | 0.42 | 0.49 | 851 |
| AA282404 | 0.02 | 0.07 | −0.29 | 0.46 | 0.58 | 852 |
| AI023336 | 0.00 | 0.24 | −0.13 | 0.28 | 0.27 | 853 |
| NM_001964 | 0.02 | −0.63 | −0.99 | 0.56 | 0.53 | 854 |
| N35603 | 0.04 | −0.51 | −0.87 | 0.51 | 0.67 | 855 |
| AI632210 | 0.00 | 0.35 | −0.01 | 0.60 | 0.26 | 856 |
| AA156454 | 0.00 | 0.37 | 0.01 | 0.34 | 0.35 | 857 |

TABLE 3-continued

Significantly under-expressed gene activities in samples of patients with infectious MODS/MOF, if compared with the gene activities of patients with non-infectious MODS/MOF.

| | | Mean normalised and transformed expression value | | Standard deviation | | |
| --- | --- | --- | --- | --- | --- | --- |
| GenBank Accession No. | p-value | Group of patients with non-infectious MOF | Group of patients with infectious MOF | Group of patients with non-infectious MOF | Group of patients with infectious MOF | SEQUENCE-ID |
| AA620836 | 0.02 | 0.24 | −0.12 | 0.51 | 0.55 | 858 |
| NM_020530 | 0.00 | 0.37 | 0.01 | 0.44 | 0.30 | 859 |
| AA928277 | 0.00 | −0.10 | −0.46 | 0.34 | 0.36 | 860 |
| NM_001559 | 0.04 | 0.37 | 0.01 | 0.73 | 0.50 | 861 |
| AA401691 | 0.00 | −0.08 | −0.44 | 0.39 | 0.38 | 862 |
| NM_015991 | 0.00 | 0.01 | −0.34 | 0.46 | 0.33 | 863 |
| N80764 | 0.00 | −0.08 | −0.43 | 0.33 | 0.43 | 864 |
| L34657 | 0.00 | 0.12 | −0.23 | 0.31 | 0.34 | 865 |
| H98244 | 0.00 | 0.24 | −0.11 | 0.39 | 0.35 | 866 |
| AA894523 | 0.00 | −0.24 | −0.59 | 0.23 | 0.29 | 867 |
| NM_013261.1 | 0.00 | 0.08 | −0.26 | 0.32 | 0.37 | 868 |
| H02254 | 0.01 | −0.39 | −0.73 | 0.40 | 0.45 | 869 |
| NM_003781.2 | 0.01 | −0.64 | −0.98 | 0.50 | 0.36 | 870 |
| NM_001243 | 0.05 | 0.78 | 0.44 | 0.51 | 0.66 | 871 |
| AA442897 | 0.01 | −0.44 | −0.78 | 0.32 | 0.46 | 872 |
| T85314 | 0.01 | −0.29 | −0.63 | 0.46 | 0.43 | 873 |
| AI658519 | 0.05 | 0.50 | 0.16 | 0.70 | 0.50 | 874 |
| AI207975 | 0.00 | −0.28 | −0.62 | 0.37 | 0.30 | 875 |
| AI536602 | 0.00 | 0.28 | −0.06 | 0.47 | 0.33 | 876 |
| NM_001541.1 | 0.00 | 0.50 | 0.16 | 0.38 | 0.27 | 877 |
| AA992540 | 0.00 | 0.14 | −0.19 | 0.31 | 0.32 | 878 |
| Z22971 | 0.01 | 0.62 | 0.29 | 0.51 | 0.39 | 879 |
| AI560847 | 0.00 | 0.36 | 0.03 | 0.23 | 0.28 | 880 |
| XM_008346 | 0.04 | 0.40 | 0.07 | 0.59 | 0.54 | 881 |
| AA015795 | 0.02 | −0.36 | −0.69 | 0.57 | 0.42 | 882 |
| R00742 | 0.00 | 0.37 | 0.04 | 0.34 | 0.33 | 883 |
| H16774 | 0.00 | 0.02 | −0.31 | 0.33 | 0.24 | 884 |
| R51373 | 0.00 | 0.15 | −0.18 | 0.31 | 0.24 | 885 |
| AI479659 | 0.00 | 0.18 | −0.14 | 0.34 | 0.29 | 886 |
| W58195 | 0.00 | −0.06 | −0.39 | 0.27 | 0.39 | 887 |
| NM_004437.1 | 0.05 | 1.06 | 0.73 | 0.47 | 0.65 | 888 |
| AA479357 | 0.00 | 0.18 | −0.15 | 0.30 | 0.21 | 889 |
| AI423518 | 0.00 | −0.25 | −0.57 | 0.29 | 0.40 | 890 |
| NM_002750 | 0.01 | −0.52 | −0.85 | 0.36 | 0.44 | 891 |
| R26444 | 0.00 | 0.00 | −0.32 | 0.27 | 0.36 | 892 |
| AA136071 | 0.00 | 0.04 | −0.29 | 0.25 | 0.34 | 893 |
| AI554459 | 0.00 | −0.02 | −0.34 | 0.39 | 0.35 | 894 |
| N51537 | 0.02 | 0.89 | 0.57 | 0.45 | 0.49 | 895 |
| NM_006068 | 0.00 | 0.62 | 0.30 | 0.35 | 0.39 | 896 |
| NM_016184 | 0.03 | 0.61 | 0.29 | 0.49 | 0.52 | 897 |
| NM_000586 | 0.03 | 0.03 | −0.29 | 0.40 | 0.54 | 898 |
| NM_003102.1 | 0.01 | −0.39 | −0.71 | 0.49 | 0.43 | 899 |
| AI264774 | 0.00 | −0.11 | −0.43 | 0.20 | 0.44 | 900 |
| N90536 | 0.01 | −0.45 | −0.77 | 0.30 | 0.45 | 901 |
| AA404342 | 0.00 | −0.29 | −0.61 | 0.36 | 0.36 | 902 |
| AI373525 | 0.00 | −0.16 | −0.48 | 0.30 | 0.25 | 903 |
| AI579907 | 0.00 | 0.07 | −0.25 | 0.38 | 0.25 | 904 |
| AA279410 | 0.00 | 0.11 | −0.21 | 0.33 | 0.26 | 905 |
| XM_038308 | 0.04 | 0.35 | 0.03 | 0.51 | 0.54 | 906 |
| NM_000879 | 0.02 | −0.01 | −0.33 | 0.37 | 0.52 | 907 |
| NM_001078) | 0.00 | 0.38 | 0.07 | 0.38 | 0.32 | 908 |
| AA781411 | 0.00 | −0.24 | −0.55 | 0.23 | 0.37 | 909 |
| R07171 | 0.00 | −0.16 | −0.48 | 0.34 | 0.37 | 910 |
| AA136273 | 0.00 | −0.10 | −0.41 | 0.26 | 0.32 | 911 |
| AI565469 | 0.01 | −0.06 | −0.37 | 0.32 | 0.41 | 912 |
| AI799767 | 0.00 | −0.12 | −0.44 | 0.35 | 0.36 | 913 |
| AI889554 | 0.00 | −0.08 | −0.39 | 0.34 | 0.36 | 914 |
| AA410301 | 0.01 | 0.77 | 0.46 | 0.35 | 0.42 | 915 |
| AA995114 | 0.04 | 1.09 | 0.79 | 0.67 | 0.40 | 916 |
| AI694444 | 0.00 | −0.40 | −0.71 | 0.26 | 0.35 | 917 |
| T98940 | 0.00 | 0.05 | −0.26 | 0.45 | 0.27 | 918 |
| R16722 | 0.00 | 0.07 | −0.23 | 0.42 | 0.23 | 919 |
| H05436 | 0.00 | 0.40 | 0.10 | 0.34 | 0.33 | 920 |
| R42778 | 0.01 | 0.39 | 0.09 | 0.45 | 0.33 | 921 |
| AI378275 | 0.00 | −0.02 | −0.33 | 0.29 | 0.40 | 922 |
| XM_083833 | 0.03 | 0.50 | 0.20 | 0.57 | 0.39 | 923 |
| R94894 | 0.03 | 1.00 | 0.70 | 0.35 | 0.55 | 924 |
| H15677 | 0.01 | −0.24 | −0.54 | 0.34 | 0.45 | 925 |

TABLE 3-continued

Significantly under-expressed gene activities in samples of patients with infectious MODS/MOF, if compared with the gene activities of patients with non-infectious MODS/MOF.

| GenBank Accession No. | p-value | Mean normalised and transformed expression value | | Standard deviation | | SEQUENCE-ID |
| --- | --- | --- | --- | --- | --- | --- |
| | | Group of patients with non-infectious MOF | Group of patients with infectious MOF | Group of patients with non-infectious MOF | Group of patients with infectious MOF | |
| AI625523 | 0.04 | 0.75 | 0.45 | 0.47 | 0.51 | 926 |
| AI627286 | 0.00 | 0.03 | −0.27 | 0.35 | 0.26 | 927 |
| NM_003807 | 0.01 | 0.08 | −0.22 | 0.35 | 0.42 | 928 |
| NM_002757 | 0.02 | 0.00 | −0.30 | 0.50 | 0.41 | 929 |
| XM_008411 | 0.02 | −0.47 | −0.77 | 0.31 | 0.51 | 930 |
| AI379294 | 0.01 | −0.06 | −0.35 | 0.45 | 0.32 | 931 |
| AI824470 | 0.00 | −0.20 | −0.49 | 0.19 | 0.42 | 932 |
| N94525 | 0.00 | 0.15 | −0.14 | 0.26 | 0.28 | 933 |
| R38432 | 0.01 | −0.03 | −0.32 | 0.27 | 0.41 | 934 |
| NM_017436.2 | 0.02 | −0.44 | −0.74 | 0.42 | 0.44 | 935 |
| AA398968 | 0.00 | −0.03 | −0.33 | 0.37 | 0.35 | 936 |
| U15085 | 0.03 | −0.89 | −1.18 | 0.47 | 0.47 | 937 |
| AI734941 | 0.01 | −0.14 | −0.43 | 0.31 | 0.41 | 938 |
| AI819159 | 0.00 | 0.44 | 0.15 | 0.39 | 0.28 | 939 |
| AA426024 | 0.02 | −0.11 | −0.40 | 0.46 | 0.42 | 940 |
| AA435854 | 0.00 | −0.33 | −0.62 | 0.21 | 0.28 | 941 |
| NM_003264 | 0.00 | 0.28 | −0.01 | 0.30 | 0.38 | 942 |
| NM_001622.1 | 0.04 | 0.01 | −0.28 | 0.41 | 0.53 | 943 |
| AI828714 | 0.04 | −0.25 | −0.55 | 0.33 | 0.54 | 944 |
| NM_006610 | 0.00 | −0.04 | −0.33 | 0.23 | 0.30 | 945 |
| AI143013 | 0.00 | −0.04 | −0.33 | 0.38 | 0.31 | 946 |
| AA428992 | 0.01 | 0.50 | 0.21 | 0.48 | 0.24 | 947 |
| R40560 | 0.02 | 0.17 | −0.12 | 0.33 | 0.44 | 948 |
| AI203091 | 0.02 | −0.44 | −0.73 | 0.28 | 0.50 | 949 |
| T92041 | 0.00 | 0.07 | −0.22 | 0.28 | 0.22 | 950 |
| AA453794 | 0.00 | 0.20 | −0.09 | 0.22 | 0.29 | 951 |
| R05804 | 0.00 | 0.18 | −0.11 | 0.22 | 0.34 | 952 |
| AA453489 | 0.01 | −0.56 | −0.85 | 0.33 | 0.37 | 953 |
| NM_006664 | 0.00 | 0.67 | 0.39 | 0.30 | 0.35 | 954 |
| AA281330 | 0.03 | 0.76 | 0.48 | 0.57 | 0.38 | 955 |
| AA452139 | 0.00 | 0.08 | −0.20 | 0.31 | 0.24 | 956 |
| R43204 | 0.00 | 0.19 | −0.09 | 0.38 | 0.21 | 957 |
| NM_012340 | 0.01 | 0.05 | −0.24 | 0.36 | 0.40 | 958 |
| NM_004778 | 0.02 | 0.00 | −0.28 | 0.43 | 0.40 | 959 |
| AA490815 | 0.01 | 0.04 | −0.24 | 0.26 | 0.44 | 960 |
| NM_022740 | 0.00 | 0.47 | 0.19 | 0.30 | 0.31 | 961 |
| AI167874 | 0.01 | 0.33 | 0.05 | 0.41 | 0.33 | 962 |
| AA149968 | 0.00 | −0.09 | −0.37 | 0.28 | 0.27 | 963 |
| XM_058179 | 0.03 | −0.04 | −0.32 | 0.58 | 0.35 | 964 |
| R07502 | 0.00 | −0.42 | −0.70 | 0.33 | 0.31 | 965 |
| NM_000752 | 0.01 | −0.27 | −0.56 | 0.48 | 0.29 | 966 |
| XM_003529 | 0.01 | 0.22 | −0.06 | 0.42 | 0.38 | 967 |
| N64541 | 0.01 | 0.13 | −0.15 | 0.44 | 0.37 | 968 |
| NM_001054 | 0.01 | 0.18 | −0.10 | 0.32 | 0.40 | 969 |
| AI499407 | 0.00 | 0.00 | −0.28 | 0.30 | 0.27 | 970 |
| NM_020056 | 0.00 | −0.05 | −0.33 | 0.32 | 0.28 | 971 |
| AA004952 | 0.01 | −0.20 | −0.48 | 0.41 | 0.31 | 972 |
| AI624610 | 0.01 | 0.09 | −0.19 | 0.34 | 0.38 | 973 |
| AA421924 | 0.04 | 0.92 | 0.64 | 0.49 | 0.44 | 974 |
| AI732550 | 0.04 | 0.03 | −0.25 | 0.51 | 0.43 | 975 |
| AI374599 | 0.02 | −0.15 | −0.43 | 0.24 | 0.47 | 976 |
| AI582909 | 0.00 | 0.34 | 0.06 | 0.21 | 0.21 | 977 |
| AI554111 | 0.00 | 0.21 | −0.07 | 0.39 | 0.21 | 978 |
| NM_001734 | 0.00 | −0.21 | −0.49 | 0.21 | 0.37 | 979 |
| AA810014 | 0.03 | 0.23 | −0.05 | 0.56 | 0.33 | 980 |
| AI373295 | 0.00 | 0.32 | 0.05 | 0.31 | 0.23 | 981 |
| XM_048555 | 0.01 | −0.20 | −0.48 | 0.38 | 0.34 | 982 |
| AA435627 | 0.00 | 0.15 | −0.13 | 0.31 | 0.26 | 983 |
| T95815 | 0.00 | 0.55 | 0.27 | 0.33 | 0.32 | 984 |
| AA426030 | 0.03 | −0.14 | −0.42 | 0.40 | 0.42 | 985 |
| AI720051 | 0.01 | −0.29 | −0.56 | 0.30 | 0.43 | 986 |
| AI278521 | 0.01 | −0.50 | −0.77 | 0.39 | 0.34 | 987 |
| N93236 | 0.01 | 0.38 | 0.10 | 0.38 | 0.34 | 988 |
| NM_015645 | 0.03 | −0.28 | −0.55 | 0.44 | 0.43 | 989 |
| AI671360 | 0.00 | 0.22 | −0.05 | 0.28 | 0.28 | 990 |
| T83666 | 0.00 | 0.13 | −0.14 | 0.36 | 0.21 | 991 |
| W02063 | 0.00 | −0.02 | −0.30 | 0.31 | 0.31 | 992 |
| AI659563 | 0.00 | 0.01 | −0.26 | 0.27 | 0.21 | 993 |

TABLE 3-continued

Significantly under-expressed gene activities in samples of patients with infectious MODS/MOF, if compared with the gene activities of patients with non-infectious MODS/MOF.

| GenBank Accession No. | p-value | Mean normalised and transformed expression value | | Standard deviation | | SEQUENCE-ID |
|---|---|---|---|---|---|---|
| | | Group of patients with non-infectious MOF | Group of patients with infectious MOF | Group of patients with non-infectious MOF | Group of patients with infectious MOF | |
| NM_139046 | 0.02 | −0.47 | −0.74 | 0.35 | 0.45 | 994 |
| AA155745 | 0.00 | 0.00 | −0.27 | 0.31 | 0.26 | 995 |
| H40035 | 0.01 | −0.32 | −0.59 | 0.28 | 0.38 | 996 |
| AA101379 | 0.00 | 0.26 | −0.02 | 0.35 | 0.31 | 997 |
| H16790 | 0.00 | 0.22 | −0.05 | 0.37 | 0.28 | 998 |
| AA011511 | 0.02 | −0.29 | −0.55 | 0.32 | 0.41 | 999 |
| AA746495 | 0.05 | 0.17 | −0.10 | 0.56 | 0.39 | 1000 |
| AA845015 | 0.00 | −0.04 | −0.30 | 0.34 | 0.26 | 1001 |
| NM_138636 | 0.05 | 0.51 | 0.24 | 0.39 | 0.52 | 1002 |
| NM_033358 | 0.01 | 0.50 | 0.24 | 0.37 | 0.37 | 1003 |
| AI650349 | 0.02 | −0.13 | −0.39 | 0.40 | 0.41 | 1004 |
| NM_001764 | 0.01 | 0.33 | 0.06 | 0.46 | 0.20 | 1005 |
| XM_006447 | 0.03 | −0.53 | −0.80 | 0.49 | 0.39 | 1006 |
| R07185 | 0.00 | 0.12 | −0.14 | 0.34 | 0.22 | 1007 |
| AA187437 | 0.00 | −0.01 | −0.27 | 0.21 | 0.26 | 1008 |
| AI621365 | 0.00 | 0.25 | −0.02 | 0.34 | 0.28 | 1009 |
| NM_020205 | 0.03 | 0.16 | −0.10 | 0.29 | 0.48 | 1010 |
| AI888390 | 0.01 | −0.89 | −1.15 | 0.31 | 0.40 | 1011 |
| AI674699 | 0.01 | −0.09 | −0.35 | 0.34 | 0.37 | 1012 |
| AI620249 | 0.02 | 0.02 | −0.24 | 0.49 | 0.27 | 1013 |
| NM_033295 | 0.02 | −0.32 | −0.58 | 0.41 | 0.39 | 1014 |
| NM_015718.1 | 0.00 | −0.08 | −0.34 | 0.23 | 0.34 | 1015 |
| N73572 | 0.05 | 0.05 | −0.21 | 0.45 | 0.42 | 1016 |
| AI420037 | 0.02 | 0.04 | −0.22 | 0.46 | 0.31 | 1017 |
| AI684431 | 0.00 | 0.28 | 0.03 | 0.32 | 0.27 | 1018 |
| AA017263 | 0.00 | 0.11 | −0.14 | 0.38 | 0.25 | 1019 |
| R45118 | 0.01 | 0.16 | −0.10 | 0.32 | 0.33 | 1020 |
| AI267659 | 0.04 | 0.01 | −0.25 | 0.21 | 0.53 | 1021 |
| AA406083 | 0.03 | 0.00 | −0.26 | 0.38 | 0.41 | 1022 |
| W48664 | 0.00 | 0.21 | −0.05 | 0.31 | 0.22 | 1023 |
| AA514450 | 0.00 | −0.38 | −0.63 | 0.26 | 0.33 | 1024 |
| AI150305 | 0.00 | 0.30 | 0.04 | 0.23 | 0.32 | 1025 |
| AA481504 | 0.03 | −0.74 | −0.99 | 0.37 | 0.42 | 1026 |
| R44840 | 0.02 | 0.22 | −0.04 | 0.45 | 0.32 | 1027 |
| AI160757 | 0.00 | 0.21 | −0.05 | 0.29 | 0.29 | 1028 |
| AA040870 | 0.00 | 0.24 | −0.02 | 0.30 | 0.30 | 1029 |
| AI342905 | 0.02 | 0.49 | 0.24 | 0.43 | 0.35 | 1030 |
| N68463 | 0.05 | 0.09 | −0.16 | 0.46 | 0.43 | 1031 |
| AA398760 | 0.00 | 0.05 | −0.20 | 0.24 | 0.23 | 1032 |
| AI798514 | 0.00 | 0.26 | 0.00 | 0.30 | 0.25 | 1033 |
| AI081725 | 0.00 | 0.18 | −0.07 | 0.31 | 0.28 | 1034 |
| AI799385 | 0.03 | 0.44 | 0.19 | 0.45 | 0.37 | 1035 |
| AA897543 | 0.04 | −0.24 | −0.49 | 0.28 | 0.49 | 1036 |
| N79807 | 0.01 | 0.18 | −0.07 | 0.33 | 0.33 | 1037 |
| AI676097 | 0.05 | 0.21 | −0.04 | 0.57 | 0.32 | 1038 |
| R46372 | 0.01 | 0.02 | −0.23 | 0.28 | 0.37 | 1039 |
| AA448817 | 0.00 | 0.26 | 0.01 | 0.28 | 0.27 | 1040 |
| AI810161 | 0.01 | 0.09 | −0.16 | 0.31 | 0.38 | 1041 |
| H80437 | 0.00 | 0.18 | −0.07 | 0.23 | 0.29 | 1042 |
| AA443664 | 0.00 | −0.02 | −0.27 | 0.29 | 0.27 | 1043 |
| NM_002957.3 | 0.01 | −0.12 | −0.37 | 0.24 | 0.37 | 1044 |
| N69363 | 0.03 | −0.35 | −0.59 | 0.37 | 0.40 | 1045 |
| NM_000552.2 | 0.01 | −0.11 | −0.36 | 0.25 | 0.34 | 1046 |
| AA455080 | 0.01 | 0.08 | −0.16 | 0.34 | 0.28 | 1047 |
| W32272 | 0.00 | −0.25 | −0.50 | 0.26 | 0.30 | 1048 |
| H38087 | 0.04 | 0.76 | 0.51 | 0.34 | 0.47 | 1049 |
| AA504336 | 0.01 | 0.26 | 0.02 | 0.32 | 0.33 | 1050 |
| H04977 | 0.00 | 0.45 | 0.21 | 0.28 | 0.28 | 1051 |
| NM_002670 | 0.05 | 0.19 | −0.06 | 0.32 | 0.50 | 1052 |
| R09417 | 0.02 | −0.07 | −0.32 | 0.31 | 0.41 | 1053 |
| AA040057 | 0.02 | −0.05 | −0.29 | 0.35 | 0.37 | 1054 |
| AI263210 | 0.01 | −0.10 | −0.34 | 0.27 | 0.33 | 1055 |
| AI264626 | 0.01 | −0.12 | −0.37 | 0.33 | 0.29 | 1056 |
| AI478847 | 0.02 | 0.11 | −0.13 | 0.34 | 0.40 | 1057 |
| AI744042 | 0.03 | −0.37 | −0.61 | 0.51 | 0.27 | 1058 |
| AA682790 | 0.02 | 0.01 | −0.23 | 0.32 | 0.40 | 1059 |
| AA629051 | 0.01 | 0.28 | 0.04 | 0.32 | 0.29 | 1060 |
| AI560242 | 0.02 | −0.23 | −0.47 | 0.36 | 0.34 | 1061 |

TABLE 3-continued

Significantly under-expressed gene activities in samples of patients with infectious MODS/MOF, if compared with the gene activities of patients with non-infectious MODS/MOF.

| GenBank Accession No. | p-value | Mean normalised and transformed expression value | | Standard deviation | | SEQUENCE-ID |
| --- | --- | --- | --- | --- | --- | --- |
| | | Group of patients with non-infectious MOF | Group of patients with infectious MOF | Group of patients with non-infectious MOF | Group of patients with infectious MOF | |
| AA035428 | 0.01 | −0.14 | −0.38 | 0.26 | 0.32 | 1062 |
| NM_014326 | 0.02 | 0.11 | −0.13 | 0.52 | 0.15 | 1063 |
| AI632740 | 0.01 | −0.16 | −0.40 | 0.31 | 0.30 | 1064 |
| AI130878 | 0.01 | 0.27 | 0.03 | 0.32 | 0.31 | 1065 |
| AI933013 | 0.01 | 0.31 | 0.07 | 0.35 | 0.26 | 1066 |
| AI086719 | 0.01 | 0.00 | −0.24 | 0.37 | 0.24 | 1067 |
| R16568 | 0.03 | 0.10 | −0.14 | 0.24 | 0.46 | 1068 |
| AA009562 | 0.01 | −0.20 | −0.44 | 0.28 | 0.33 | 1069 |
| AI015069 | 0.01 | 0.04 | −0.20 | 0.32 | 0.34 | 1070 |
| AA291486 | 0.02 | −0.26 | −0.49 | 0.31 | 0.36 | 1071 |
| H65288 | 0.03 | −0.13 | −0.37 | 0.26 | 0.46 | 1072 |
| W86767 | 0.02 | 0.07 | −0.17 | 0.20 | 0.42 | 1073 |
| H65331 | 0.01 | 0.55 | 0.31 | 0.33 | 0.33 | 1074 |
| AA478985 | 0.04 | −0.12 | −0.36 | 0.20 | 0.51 | 1075 |
| H11274 | 0.02 | −0.02 | −0.26 | 0.28 | 0.40 | 1076 |
| AA044225 | 0.00 | −0.09 | −0.33 | 0.31 | 0.22 | 1077 |
| AI801415 | 0.00 | −0.08 | −0.32 | 0.32 | 0.23 | 1078 |
| AA846527 | 0.00 | −0.14 | −0.37 | 0.24 | 0.25 | 1079 |
| R56890 | 0.01 | −0.04 | −0.28 | 0.25 | 0.34 | 1080 |
| AI921525 | 0.03 | −0.06 | −0.29 | 0.36 | 0.40 | 1081 |
| AA405485 | 0.02 | 0.11 | −0.13 | 0.40 | 0.33 | 1082 |
| AA845635 | 0.00 | −0.03 | −0.26 | 0.31 | 0.26 | 1083 |
| AI150418 | 0.01 | 0.07 | −0.17 | 0.23 | 0.33 | 1084 |
| XM_049849 | 0.02 | 0.55 | 0.32 | 0.32 | 0.37 | 1085 |
| AA406573 | 0.00 | 0.20 | −0.03 | 0.33 | 0.23 | 1086 |
| AA043930 | 0.01 | −0.26 | −0.49 | 0.27 | 0.35 | 1087 |
| AI125496 | 0.01 | −0.30 | −0.53 | 0.29 | 0.33 | 1088 |
| AI654739 | 0.02 | −0.06 | −0.29 | 0.31 | 0.35 | 1089 |
| AA398320 | 0.01 | −0.32 | −0.56 | 0.37 | 0.30 | 1090 |
| NM_002155 | 0.04 | 0.48 | 0.25 | 0.36 | 0.43 | 1091 |
| AA505872 | 0.01 | 0.71 | 0.48 | 0.31 | 0.34 | 1092 |
| NM_016610 | 0.02 | 0.24 | 0.00 | 0.20 | 0.43 | 1093 |
| AA703200 | 0.00 | −0.13 | −0.36 | 0.26 | 0.29 | 1094 |
| R44493 | 0.00 | 0.04 | −0.19 | 0.24 | 0.23 | 1095 |
| XM_046575 | 0.04 | −0.14 | −0.38 | 0.40 | 0.40 | 1096 |
| AI275613 | 0.03 | 0.24 | 0.00 | 0.44 | 0.30 | 1097 |
| AI308602 | 0.04 | 0.19 | −0.05 | 0.38 | 0.40 | 1098 |
| R44328 | 0.01 | 0.24 | 0.01 | 0.30 | 0.30 | 1099 |
| R00206 | 0.00 | 0.07 | −0.16 | 0.23 | 0.31 | 1100 |
| NM_002456 | 0.01 | 0.02 | −0.21 | 0.37 | 0.25 | 1101 |
| AI699371 | 0.03 | −0.18 | −0.41 | 0.46 | 0.28 | 1102 |
| AA935135 | 0.03 | 0.21 | −0.02 | 0.41 | 0.33 | 1103 |
| AA702529 | 0.02 | 0.06 | −0.17 | 0.40 | 0.27 | 1104 |
| AI568023 | 0.02 | −0.19 | −0.42 | 0.36 | 0.30 | 1105 |
| NM_002768 | 0.01 | −0.65 | −0.88 | 0.27 | 0.31 | 1106 |
| AA687208 | 0.02 | −0.32 | −0.55 | 0.24 | 0.39 | 1107 |
| AI221524 | 0.04 | 0.47 | 0.25 | 0.49 | 0.31 | 1108 |
| AA813007 | 0.01 | 0.09 | −0.13 | 0.24 | 0.33 | 1109 |
| AA421326 | 0.02 | −0.33 | −0.55 | 0.28 | 0.38 | 1110 |
| AA922397 | 0.01 | 0.06 | −0.17 | 0.19 | 0.33 | 1111 |
| R51857 | 0.03 | 0.90 | 0.67 | 0.40 | 0.30 | 1112 |
| NM_006564 | 0.00 | −0.22 | −0.44 | 0.33 | 0.21 | 1113 |
| AA807376 | 0.01 | 0.39 | 0.17 | 0.31 | 0.25 | 1114 |
| AA812763 | 0.04 | −0.45 | −0.68 | 0.36 | 0.37 | 1115 |
| AA528169 | 0.02 | 0.34 | 0.12 | 0.37 | 0.32 | 1116 |
| AI804325 | 0.01 | −0.14 | −0.36 | 0.32 | 0.24 | 1117 |
| T70330 | 0.04 | −0.10 | −0.33 | 0.30 | 0.41 | 1118 |
| NM_001766 | 0.03 | 0.30 | 0.08 | 0.39 | 0.35 | 1119 |
| AI696956 | 0.01 | −0.12 | −0.34 | 0.40 | 0.23 | 1120 |
| AI459174 | 0.01 | −0.05 | −0.27 | 0.30 | 0.25 | 1121 |
| R35639 | 0.01 | −0.03 | −0.25 | 0.17 | 0.37 | 1122 |
| W69774 | 0.01 | −0.02 | −0.24 | 0.21 | 0.30 | 1123 |
| AA054265 | 0.05 | 0.37 | 0.15 | 0.40 | 0.38 | 1124 |
| AI382995 | 0.01 | 0.19 | −0.03 | 0.29 | 0.25 | 1125 |
| AI218303 | 0.01 | 0.00 | −0.22 | 0.31 | 0.26 | 1126 |
| AI624954 | 0.01 | −0.18 | −0.40 | 0.28 | 0.31 | 1127 |
| AA759254 | 0.05 | −0.08 | −0.30 | 0.49 | 0.29 | 1128 |
| AI682979 | 0.02 | 0.03 | −0.19 | 0.22 | 0.37 | 1129 |

TABLE 3-continued

Significantly under-expressed gene activities in samples of patients with infectious MODS/MOF, if compared with the gene activities of patients with non-infectious MODS/MOF.

| GenBank Accession No. | p-value | Mean normalised and transformed expression value | | Standard deviation | | SEQUENCE-ID |
|---|---|---|---|---|---|---|
| | | Group of patients with non-infectious MOF | Group of patients with infectious MOF | Group of patients with non-infectious MOF | Group of patients with infectious MOF | |
| XM_001754 | 0.01 | 0.18 | −0.03 | 0.31 | 0.28 | 1130 |
| AI187401 | 0.00 | −0.01 | −0.23 | 0.21 | 0.22 | 1131 |
| AA452113 | 0.01 | 0.24 | 0.02 | 0.25 | 0.30 | 1132 |
| AI656210 | 0.04 | −0.48 | −0.70 | 0.30 | 0.40 | 1133 |
| N29999 | 0.01 | 0.21 | 0.00 | 0.22 | 0.34 | 1134 |
| N68557 | 0.01 | 0.00 | −0.21 | 0.19 | 0.32 | 1135 |
| AI689672 | 0.02 | −0.08 | −0.29 | 0.42 | 0.19 | 1136 |
| AA730310 | 0.00 | −0.07 | −0.28 | 0.25 | 0.22 | 1137 |
| AI431324 | 0.01 | −0.20 | −0.42 | 0.39 | 0.22 | 1138 |
| NM_000066 | 0.04 | −0.11 | −0.32 | 0.31 | 0.40 | 1139 |
| XM_034219 | 0.01 | 0.01 | −0.21 | 0.30 | 0.29 | 1140 |
| R43258 | 0.04 | 0.27 | 0.05 | 0.49 | 0.23 | 1141 |
| AI431293 | 0.00 | 0.07 | −0.15 | 0.25 | 0.22 | 1142 |
| R80259 | 0.04 | −0.49 | −0.70 | 0.22 | 0.38 | 1143 |
| AI126520 | 0.00 | 0.13 | −0.08 | 0.22 | 0.21 | 1144 |
| AA937226 | 0.00 | 0.02 | −0.19 | 0.25 | 0.26 | 1145 |
| AI191762 | 0.03 | −0.22 | −0.43 | 0.30 | 0.36 | 1146 |
| AA400470 | 0.00 | −0.10 | −0.31 | 0.34 | 0.17 | 1147 |
| NM_000063 | 0.01 | −0.17 | −0.38 | 0.29 | 0.23 | 1148 |
| H73962 | 0.01 | −0.11 | −0.32 | 0.22 | 0.30 | 1149 |
| AA626313 | 0.01 | −0.06 | −0.27 | 0.23 | 0.30 | 1150 |
| AI553630 | 0.03 | 0.13 | −0.08 | 0.36 | 0.31 | 1151 |
| NM_000257.1 | 0.01 | 0.37 | 0.16 | 0.29 | 0.25 | 1152 |
| N68456 | 0.03 | 0.33 | 0.12 | 0.27 | 0.36 | 1153 |
| XM_054837 | 0.01 | 0.24 | 0.04 | 0.24 | 0.27 | 1154 |
| AI696558 | 0.04 | −0.49 | −0.70 | 0.38 | 0.33 | 1155 |
| AI299876 | 0.05 | 0.03 | −0.18 | 0.36 | 0.37 | 1156 |
| NM_006378 | 0.03 | 0.65 | 0.44 | 0.28 | 0.36 | 1157 |
| AI376955 | 0.02 | −0.56 | −0.76 | 0.31 | 0.33 | 1158 |
| AA025573 | 0.01 | −0.24 | −0.45 | 0.33 | 0.25 | 1159 |
| T99196 | 0.02 | 0.14 | −0.07 | 0.34 | 0.29 | 1160 |
| XM_005637 | 0.05 | 0.25 | 0.05 | 0.19 | 0.45 | 1161 |
| AI597729 | 0.04 | −0.01 | −0.21 | 0.24 | 0.41 | 1162 |
| H78135 | 0.02 | 0.04 | −0.17 | 0.29 | 0.33 | 1163 |
| AI695029 | 0.01 | 0.04 | −0.16 | 0.27 | 0.25 | 1164 |
| AA004279 | 0.02 | −0.18 | −0.39 | 0.21 | 0.34 | 1165 |
| AA844020 | 0.03 | 0.33 | 0.12 | 0.30 | 0.33 | 1166 |
| AI332536 | 0.00 | −0.12 | −0.33 | 0.20 | 0.18 | 1167 |
| AI383368 | 0.03 | −0.40 | −0.61 | 0.21 | 0.38 | 1168 |
| AA423883 | 0.00 | −0.06 | −0.26 | 0.17 | 0.28 | 1169 |
| R36006 | 0.02 | −0.06 | −0.26 | 0.30 | 0.29 | 1170 |
| AI911837 | 0.02 | −0.05 | −0.26 | 0.30 | 0.31 | 1171 |
| AI696820 | 0.03 | −0.37 | −0.57 | 0.32 | 0.34 | 1172 |
| H30516 | 0.02 | −0.17 | −0.37 | 0.22 | 0.34 | 1173 |
| AI926561 | 0.01 | 0.02 | −0.18 | 0.37 | 0.20 | 1174 |
| H61449 | 0.02 | −0.25 | −0.45 | 0.24 | 0.32 | 1175 |
| AA410338 | 0.02 | −0.18 | −0.38 | 0.37 | 0.26 | 1176 |
| AA485229 | 0.00 | 0.05 | −0.15 | 0.18 | 0.18 | 1177 |
| AA044828 | 0.01 | −0.01 | −0.21 | 0.22 | 0.31 | 1178 |
| R07278 | 0.03 | 0.00 | −0.20 | 0.15 | 0.39 | 1179 |
| AI687656 | 0.02 | −0.22 | −0.42 | 0.28 | 0.28 | 1180 |
| AI912316 | 0.03 | 0.21 | 0.01 | 0.42 | 0.24 | 1181 |
| AA017301 | 0.00 | −0.07 | −0.27 | 0.18 | 0.26 | 1182 |
| AA059314 | 0.05 | 0.13 | −0.07 | 0.26 | 0.40 | 1183 |
| NM_024302.2 | 0.04 | 0.20 | 0.00 | 0.29 | 0.35 | 1184 |
| AA446463 | 0.02 | −0.15 | −0.34 | 0.29 | 0.29 | 1185 |
| NM_002747 | 0.01 | 0.19 | −0.01 | 0.24 | 0.24 | 1186 |
| AA446316 | 0.02 | 0.03 | −0.17 | 0.30 | 0.29 | 1187 |
| NM_052813) | 0.05 | −0.22 | −0.42 | 0.39 | 0.30 | 1188 |
| AA731532 | 0.00 | −0.24 | −0.43 | 0.18 | 0.24 | 1189 |
| R00307 | 0.04 | 0.16 | −0.03 | 0.45 | 0.20 | 1190 |
| AI924296 | 0.03 | −0.08 | −0.28 | 0.19 | 0.36 | 1191 |
| AI017741 | 0.01 | 0.07 | −0.12 | 0.29 | 0.21 | 1192 |
| AI619681 | 0.01 | −0.18 | −0.37 | 0.17 | 0.29 | 1193 |
| AA400967 | 0.01 | 0.25 | 0.06 | 0.30 | 0.22 | 1194 |
| NM_000680.1 | 0.01 | 0.28 | 0.09 | 0.20 | 0.28 | 1195 |
| AI732878 | 0.00 | −0.09 | −0.28 | 0.16 | 0.16 | 1196 |
| XM_006454 | 0.02 | −0.08 | −0.27 | 0.34 | 0.24 | 1197 |

TABLE 3-continued

Significantly under-expressed gene activities in samples of patients with infectious MODS/MOF, if compared with the gene activities of patients with non-infectious MODS/MOF.

| | | Mean normalised and transformed expression value | | Standard deviation | | |
| --- | --- | --- | --- | --- | --- | --- |
| GenBank Accession No. | p-value | Group of patients with non-infectious MOF | Group of patients with infectious MOF | Group of patients with non-infectious MOF | Group of patients with infectious MOF | SEQUENCE-ID |
| AI688916 | 0.03 | 0.02 | −0.17 | 0.32 | 0.29 | 1198 |
| T79834 | 0.01 | 0.09 | −0.10 | 0.25 | 0.27 | 1199 |
| AI015693 | 0.01 | −0.01 | −0.20 | 0.20 | 0.27 | 1200 |
| R50755 | 0.00 | −0.01 | −0.20 | 0.19 | 0.19 | 1201 |
| W44337 | 0.04 | 0.05 | −0.13 | 0.18 | 0.39 | 1202 |
| H23267 | 0.03 | −0.37 | −0.55 | 0.26 | 0.31 | 1203 |
| AA101850 | 0.02 | −0.12 | −0.30 | 0.34 | 0.21 | 1204 |
| AI628322 | 0.05 | −0.03 | −0.22 | 0.37 | 0.28 | 1205 |
| R94207 | 0.02 | 0.13 | −0.06 | 0.26 | 0.28 | 1206 |
| NM_004347 | 0.03 | 0.32 | 0.14 | 0.35 | 0.27 | 1207 |
| AA960802 | 0.05 | 0.14 | −0.04 | 0.37 | 0.29 | 1208 |
| NM_052962 | 0.02 | −0.42 | −0.60 | 0.26 | 0.25 | 1209 |
| T91946 | 0.04 | 0.14 | −0.05 | 0.29 | 0.33 | 1210 |
| AA531564 | 0.04 | −0.14 | −0.32 | 0.37 | 0.26 | 1211 |
| R96155 | 0.01 | 0.00 | −0.18 | 0.28 | 0.21 | 1212 |
| AI825491 | 0.02 | −0.07 | −0.25 | 0.19 | 0.29 | 1213 |
| N53973 | 0.02 | 0.01 | −0.17 | 0.22 | 0.31 | 1214 |
| NM_001544 | 0.01 | 0.10 | −0.08 | 0.27 | 0.22 | 1215 |
| AA702731 | 0.00 | −0.16 | −0.34 | 0.19 | 0.23 | 1216 |
| AI554655 | 0.05 | −0.04 | −0.22 | 0.23 | 0.36 | 1217 |
| H17495 | 0.04 | 0.50 | 0.32 | 0.29 | 0.31 | 1218 |
| AI209185 | 0.02 | −0.24 | −0.42 | 0.16 | 0.31 | 1219 |
| AA031813 | 0.03 | −0.15 | −0.33 | 0.29 | 0.27 | 1220 |
| NM_004166 | 0.04 | −0.37 | −0.54 | 0.35 | 0.27 | 1221 |
| AA461044 | 0.02 | 0.06 | −0.11 | 0.21 | 0.31 | 1222 |
| N45328 | 0.05 | −0.12 | −0.29 | 0.32 | 0.30 | 1223 |
| N64446 | 0.03 | −0.24 | −0.42 | 0.24 | 0.32 | 1224 |
| AI633617 | 0.01 | −0.05 | −0.22 | 0.23 | 0.24 | 1225 |
| R45159 | 0.03 | 0.22 | 0.05 | 0.32 | 0.24 | 1226 |
| R60898 | 0.00 | 0.13 | −0.04 | 0.18 | 0.17 | 1227 |
| AI621170 | 0.03 | −0.05 | −0.22 | 0.30 | 0.27 | 1228 |
| N99049 | 0.01 | 0.16 | −0.01 | 0.31 | 0.19 | 1229 |
| H18651 | 0.01 | 0.19 | 0.02 | 0.24 | 0.22 | 1230 |
| AA568582 | 0.04 | 0.02 | −0.15 | 0.30 | 0.28 | 1231 |
| AA026871 | 0.03 | −0.02 | −0.19 | 0.37 | 0.20 | 1232 |
| AI559626 | 0.01 | −0.11 | −0.28 | 0.23 | 0.21 | 1233 |
| AA443545 | 0.03 | 0.46 | 0.29 | 0.27 | 0.28 | 1234 |
| R43339 | 0.04 | 0.22 | 0.06 | 0.36 | 0.23 | 1235 |
| AA007369 | 0.04 | −0.16 | −0.33 | 0.28 | 0.30 | 1236 |
| AA960982 | 0.01 | 0.25 | 0.08 | 0.26 | 0.22 | 1237 |
| AA481399 | 0.01 | 0.01 | −0.16 | 0.30 | 0.18 | 1238 |
| AA280005 | 0.02 | −0.17 | −0.34 | 0.23 | 0.26 | 1239 |
| NM_005666 | 0.01 | 0.36 | 0.19 | 0.26 | 0.20 | 1240 |
| NM_000491 | 0.03 | 0.08 | −0.09 | 0.32 | 0.24 | 1241 |
| AA844053 | 0.03 | −0.12 | −0.28 | 0.22 | 0.26 | 1242 |
| R49384 | 0.01 | −0.05 | −0.22 | 0.24 | 0.21 | 1243 |
| AI698289 | 0.01 | −0.16 | −0.33 | 0.23 | 0.21 | 1244 |
| AI680467 | 0.04 | −0.09 | −0.26 | 0.23 | 0.31 | 1245 |
| M90391 | 0.03 | −0.11 | −0.28 | 0.27 | 0.23 | 1246 |
| AF218727 | 0.05 | 0.18 | 0.02 | 0.25 | 0.31 | 1247 |
| H22946 | 0.04 | −0.44 | −0.60 | 0.27 | 0.29 | 1248 |
| N49285 | 0.03 | −0.51 | −0.67 | 0.23 | 0.28 | 1249 |
| N74903 | 0.01 | 0.17 | 0.01 | 0.21 | 0.22 | 1250 |
| NM_001066.2 | 0.04 | 0.14 | −0.02 | 0.23 | 0.30 | 1251 |
| NM_021805 | 0.02 | 0.05 | −0.11 | 0.29 | 0.21 | 1252 |
| NM_004590 | 0.04 | 0.26 | 0.10 | 0.27 | 0.27 | 1253 |
| AA482392 | 0.01 | −0.19 | −0.35 | 0.25 | 0.20 | 1254 |
| AA131826 | 0.01 | −0.04 | −0.20 | 0.26 | 0.17 | 1255 |
| AA947111 | 0.02 | 0.07 | −0.09 | 0.17 | 0.27 | 1256 |
| AI159796 | 0.04 | −0.13 | −0.28 | 0.20 | 0.28 | 1257 |
| AF086537 | 0.05 | 0.15 | −0.01 | 0.32 | 0.24 | 1258 |
| AI147932 | 0.00 | 0.13 | −0.03 | 0.23 | 0.16 | 1259 |
| AA460956 | 0.04 | 0.11 | −0.04 | 0.30 | 0.24 | 1260 |
| AA398249 | 0.03 | −0.11 | −0.27 | 0.23 | 0.26 | 1261 |
| H08161 | 0.04 | −0.23 | −0.39 | 0.23 | 0.28 | 1262 |
| AA281734 | 0.03 | −0.12 | −0.28 | 0.31 | 0.19 | 1263 |
| AA628488 | 0.04 | −0.18 | −0.33 | 0.20 | 0.30 | 1264 |
| AA430519 | 0.04 | −0.06 | −0.21 | 0.22 | 0.26 | 1265 |

TABLE 3-continued

Significantly under-expressed gene activities in samples of patients with infectious MODS/MOF, if compared with the gene activities of patients with non-infectious MODS/MOF.

| GenBank Accession No. | p-value | Mean normalised and transformed expression value | | Standard deviation | | SEQUENCE-ID |
| | | Group of patients with non-infectious MOF | Group of patients with infectious MOF | Group of patients with non-infectious MOF | Group of patients with infectious MOF | |
|---|---|---|---|---|---|---|
| AA468113 | 0.05 | −0.16 | −0.31 | 0.29 | 0.25 | 1266 |
| AI424466 | 0.04 | 0.06 | −0.10 | 0.26 | 0.24 | 1267 |
| AI190760 | 0.04 | 0.04 | −0.11 | 0.29 | 0.23 | 1268 |
| N89992 | 0.01 | −0.06 | −0.21 | 0.23 | 0.18 | 1269 |
| AA046092 | 0.01 | 0.10 | −0.05 | 0.16 | 0.21 | 1270 |
| W35358 | 0.02 | 0.05 | −0.10 | 0.22 | 0.20 | 1271 |
| AA398341 | 0.04 | −0.19 | −0.33 | 0.27 | 0.23 | 1272 |
| H01969 | 0.05 | −0.09 | −0.24 | 0.32 | 0.20 | 1273 |
| AA970008 | 0.05 | −0.34 | −0.48 | 0.32 | 0.21 | 1274 |
| R89846 | 0.01 | 0.14 | −0.01 | 0.20 | 0.20 | 1275 |
| H18639 | 0.04 | 0.13 | −0.02 | 0.26 | 0.24 | 1276 |
| AI016342 | 0.02 | 0.02 | −0.12 | 0.18 | 0.22 | 1277 |
| NM_002184 | 0.04 | −0.23 | −0.37 | 0.17 | 0.28 | 1278 |
| NM_001643.1 | 0.03 | 0.13 | −0.01 | 0.19 | 0.26 | 1279 |
| AA280029 | 0.04 | −0.14 | −0.28 | 0.28 | 0.22 | 1280 |
| AA927949 | 0.00 | 0.17 | 0.02 | 0.16 | 0.14 | 1281 |
| AA625552 | 0.04 | 0.05 | −0.09 | 0.28 | 0.20 | 1282 |
| AA458912 | 0.03 | −0.23 | −0.37 | 0.24 | 0.23 | 1283 |
| AI188025 | 0.02 | 0.29 | 0.15 | 0.21 | 0.22 | 1284 |
| XM_007417 | 0.02 | 0.00 | −0.14 | 0.21 | 0.19 | 1285 |
| AA019529 | 0.03 | −0.29 | −0.42 | 0.22 | 0.22 | 1286 |
| AA401542 | 0.04 | −0.09 | −0.22 | 0.17 | 0.25 | 1287 |
| AI478746 | 0.04 | 0.00 | −0.13 | 0.23 | 0.22 | 1288 |
| AA291522 | 0.01 | −0.33 | −0.47 | 0.14 | 0.22 | 1289 |
| AI493122 | 0.05 | 0.16 | 0.03 | 0.25 | 0.22 | 1290 |
| AI203665 | 0.02 | 0.11 | −0.02 | 0.22 | 0.18 | 1291 |
| R74060 | 0.05 | −0.15 | −0.28 | 0.20 | 0.24 | 1292 |
| AI185721 | 0.04 | −0.25 | −0.37 | 0.22 | 0.19 | 1293 |
| AA437106 | 0.05 | 0.10 | −0.02 | 0.23 | 0.20 | 1294 |
| NM_139208 | 0.04 | −0.07 | −0.18 | 0.22 | 0.20 | 1295 |
| AI922221 | 0.05 | −0.02 | −0.14 | 0.20 | 0.20 | 1296 |
| AA412418 | 0.05 | −0.26 | −0.37 | 0.19 | 0.18 | 1297 |

The changes characterized in Tables 2 and 3 can be used for the inventive process.

The GenBank Accession Numbers indicated in Tables 2 and 3 of the individual sequences are associated with the attached sequence listing, itemized or in detail with respectively one sequence (SEQ ID NO: 1 up through SEQ ID NO: 1297).

REFERENCES

1. Natanson C (1997) Anti-inflammatory therapies to treat sepsis and septic shock: A reassessment. Crit Care Med 25: 1095-1099
2. Geiger K (1995) Frühparameter für Multiorgandysfunktionssyndrom (early parameters for multiple organ dysfunction syndrome). in Hartenauer U (ed.) Sepsis in der Frühphase München MMV Medizin Verlag 19-25
3. Knaus W A, Draper E A, Wagner D P, Zimmermann J E (1985) Prognosis in acute organ-system failure. Ann Surg 202: 658-693
4. Goris R I, Bockhorst T P, Nuytinck J K S (1995) Multiple organ failure. Arch Surg 120:1109-1115
5. Vincent J L, Moreno R, Takala J, et al. (1996) The SOFA (Sepsis-related Organ Failure Assessment) score to describe organ dysfunction/failure. On behalf of the Working Group on Sepsis-Related Problems of the European Society of Intensive Care Medicine, Intensive Care Med. July 22(7):707-10.
6. Pfeiffer L, Ehrhardt N, Kretschmar R, et al. (1996) Endotoxinämie und Multiorganversagen nach Polytrauma (endotoxemia and multiple organ failure upon polytrauma). Anaesthesiol Reanimat 21: 91-96
7. Schlag G, Redl H (1993) Organ in shock, early organ failure, late organ failure, in Schlag G and Redl H (eds.) Pathophysiology of shock, sepsis, and organ failure Berlin Heidelberg Springer-Verlag, 1-4
8. Bone R C, Balk R A, Cerra F B, et al. (1992) The ACCP/SCCM Consensus Conference Committee (1992) Definitions for Sepsis and organ failure and guidelines for the use of innovative therapies in Sepsis. Chest 101:1656-1662; und Crit Care Med 1992; 20: 864-874.
9. Levy M M, Fink M, Marshall J C, et al. (2003) For the International Sepsis Definitions Conference: 2001 SCCM/ESICM/ACCP/ATS/SIS International Sepsis Definitions Conference. Crit Care Med. April; 31(4):1250-6
11. Marik P E. (1993) Gastric intramucosal pH. A better predictor of multiorgan dysfuction syndrome and death than oxygen derived variables in patients with sepsis. CHEST 104: 225-229
12. Bernardin G, Pradier C, Tiger F, et al. (1996) Blood pressure and arterial lactate level are early indicators of short-term survival in human septic shock. Intensiv Care Med 22: 17-25;
13. Marecaux G, Pinsky M R, Dupont E, et al. (1996) Blood lactate levels are better prognostic indicators than TNF and IL-6 levels in patients with septic shock. Intensiv Care Med 22: 404-408

14. Duswald K H, Jochum M, Schramm W, Fritz H (1985) Released granulocytic elastase: an indicator of pathobiochemical alterations in septicemia after abdominal surgery. Surgery 98: 892-899
15. Nuytinck J K S, Goris R I, Redl H, et al. (1986) Posttraumatic complications and inflammatory mediators. Arch Surg 121: 886-890
16. Nast-Kolb D, Jochum M, Waydlas C, et al. (1991) Die Wertigkeit biochemischer Faktoren beim Polytrauma. (Valence of biochemical factors with polytrauma). Hefte Unfallheilkunde 215: 215
17. Hack C E, de Groot E R, Felt-Bersma R J, et al. (1989): Increased plasma levels of interleukin-6 in sepsis" Blood 74: 1704-1710
18. Patel R T, Deen K I, Youngs D, et al. (1994) Interleukin 6 is a prognostic indicator of outcome in severe intra-abdominal sepsis. Br J Surg 81:1306-1308
19. Southern E M (1974) An improved method for transferring nucleotides from electrophoresis strips to thin layers of ion-exchange cellulose. Anal Biochem 62:317-318
20. Gillespie D, Spiegelman S (1965) A quantitative assay for DNA-RNA hybrids with DNA immobilized on a membrane. J Mol Biol 12:829-842
21. Lennon G G, Lehrach H (1991) Hybridization analyses of arrayed cDNA libraries. Trends Genet 7: 314-317
22. Kafatos F C, Jones C W, Efstratiadis A (1979) Determination of nucleic acid sequence homologies and relative concentrations by a dot hybridization procedure. Nucl Acid Res 7:1541-1552
23. Fodor S P, Read J L, Pirrung M C, Stryer L, Lu A T, Solas D (1991) Light-directed, spatially addressable parallel chemical synthesis. Science 251:767-773
24. Pease A C, Solas D, Sullivan E J, Cronin M T, Holmes C P, Fodor S P (1994) Light-generated oligonucleotide arrays for rapid DNA sequence analysis. Proc Natl Acad Sci USA 91:5022-5026
25. Schena M, Shalon D, Davis R W, Brown P O (1995) Quantitative monitoring of gene expression patterns with a complementary DNA microarray. Science 270:467-470
26. Golub T R, Slonim D K, Tamayo P, et al. (1999) Molecular classification of cancer: class discovery and class prediction by gene expression monitoring. Science 286:531-537
27. Alizadeh A A, Eisen M B, Davis R E, et al. (2000) Distinct types of diffuse large B-cell lymphoma identified by gene expression profiling. Nature 403:503-51
28. Feezor R J, Baker H V, Xiao W, et al. (2004) Genomic and Proteomic Determinants of outcome in patients undergoing thoracoabdominal aortic aneurysm repair. Journal of Immunology 172 (11): 7103-7109
29. Huber W, Heydebreck A, Sueltmann H, et al. (2003) Parameter estimation for the calibration and variance stabilization of microarray data. Stat. Appl. in Gen. and Mol. Biol. Vol. 2, Issue 1, Article 3

The invention claimed is:

1. A method of differentiating between the non-infectious and infectious causes of multiple organ failure in a human subject, comprising:
   a. isolating sample RNA from a blood sample from said human subject;
   b. selecting at least two genes and/or gene fragments specific for differentiating non-infectious and infectious causes of multiple organ failure from a group consisting of: SEQ ID NO. 1 to SEQ ID NO. 1297 as well as gene fragments thereof with at least 20-2000 nucleotides;
   c. quantitatively measuring the level of expression of said at least two genes and/or gene fragment;
   d. comparing the quantitative data of the expression level of said at least two genes and/or gene fragments against an expression level of said at least two genes and/or gene fragments of a patient with non-infectious multiple organ failure; and
   e. in the case that said genes and/or gene fragments selected from the group consisting of SEQ ID NO:1-721 are expressed more in the sample than in the patient with non-infectious multiple organ failure, diagnosing the human subject as having risk of infectious multiple organ failure and in the case that said at least two genes and/or gene fragments selected from the group consisting of SEQ ID NO: 722-1297 are decreased more in the sample than in the patient with non-infectious multiple organ failure, diagnosing the human subject as having risk of infectious multiple organ failure.

2. The method according to claim 1, comprising assessing the course of disease in non-infectious and infectious multiple organ failure during therapy.

3. The method according to claim 1, comprising classification of patients as to non-infectious or infectious causes of multiple organ failure.

4. The method according to claim 3, wherein said method serves as inclusion criterion or exclusion criterion of patients with non-infectious or infectious causes of multiple organ failure in clinical studies of stages 2-4.

5. The method according to claim 1, further comprising generation of gene activity data for further electronic processing.

6. The method according to claim 5, wherein the gene activity data are used for the production of software for the description of the individual prognosis of a patient, for diagnostic purposes and/or patient data management systems.

7. The method according to claim 5, wherein the gene activity data are used for the production of clinical expert systems and/or for modelling of cellular signal transmission paths.

8. The method according to claim 1, comprising using a specific gene and/or gene fragment for the generation of gene expression profiles, the gene and/or gene fragment being

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US08476200B2). An electronic copy of the "Sequence Listing" will also be available from the USPTO upon request and payment of the fee set forth in 37 CFR 1.19(b)(3).

selected from a group consisting of SEQ ID NO. 1 to SEQ ID NO. 1297 as well as gene fragments thereof with at least 20-2000 nucleotides.

9. The method according to claim 8, wherein the gene fragments comprise 20-200 nucleotides.

10. The method according to claim 8, wherein the gene fragments comprise 20-80 nucleotides.

11. The method according to claim 1, wherein the gene expression profiles are ascertained by means of hybridizing methods.

12. The method according to claim 11, wherein the hybridizing methods are conducted on microarrays.

13. The method according to claim 1, wherein at least 2 to 100 different genes and/or gene fragments are used.

14. The method according to claim 1, wherein at least 200 different genes and/or gene fragments are used.

15. The method according to claim 1, wherein at least 200 to 500 different genes and/or gene fragments are used.

16. The method according to claim 1, wherein at least 500 to 1000 different genes and/or gene fragments are used.

17. The method according to claim 1, wherein at least 1000 to 2000 different genes and/or gene fragments are used.

18. The method according to claim 1, wherein the gene activity is determined by hybridisation-independent methods, in particular by enzymatic and/or chemical hydrolysis and/or amplification methods, preferably PCR, subsequent quantification of nucleic acids and/or of derivates and/or fragments of same.

19. The method according to claim 1, wherein the sample is selected from the group consisting of body fluids, in particular blood, liquor, urine, ascitic fluid, seminal fluid, saliva, puncture fluid, cell content, or a mixture thereof.

20. The method according to claim 1, wherein cell samples are subjected to lytic treatment in order to free their cell contents.

* * * * *